United States Patent
Razeghi

(10) Patent No.: US 9,917,418 B2
(45) Date of Patent: Mar. 13, 2018

(54) MONOLITHICAL WIDELY TUNABLE QUANTUM CASCADE LASER DEVICES

(71) Applicant: Northwestern University, Evanston, IL (US)

(72) Inventor: Manijeh Razeghi, Wilmette, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/338,753

(22) Filed: Oct. 31, 2016

(65) Prior Publication Data

US 2017/0194765 A1 Jul. 6, 2017

Related U.S. Application Data

(60) Provisional application No. 62/275,351, filed on Jan. 6, 2016.

(51) Int. Cl.
*G01J 5/02* (2006.01)
*H01S 5/0687* (2006.01)
(Continued)

(52) U.S. Cl.
CPC ....... *H01S 5/0687* (2013.01); *G01N 21/3504* (2013.01); *G01N 21/39* (2013.01); *G02B 6/00* (2013.01); *H01S 5/028* (2013.01); *H01S 5/06258* (2013.01); *H01S 5/1028* (2013.01); *H01S 5/3401* (2013.01); *H01S 5/34313* (2013.01); *H01S 5/4037* (2013.01); *G01N 2021/3595* (2013.01); *G01N 2021/399* (2013.01); *H01S 5/026* (2013.01); *H01S 5/0208* (2013.01); *H01S 5/0287* (2013.01); *H01S 5/1209* (2013.01); *H01S 5/22* (2013.01); *H01S 5/4012* (2013.01); *H01S 5/4087* (2013.01)

(58) Field of Classification Search
CPC .... H01S 5/026; H01S 5/06256; H01S 5/4087; H01S 5/1096; H01S 5/125; H01S 5/141; H01S 5/06258; H01S 5/34; H01S 5/1237; H01S 5/2031; H01S 5/34; H01S 5/1092; H01S 5/1228; H01S 5/187; G01N 21/3504
USPC ...................................... 250/339.08
See application file for complete search history.

(56) References Cited

U.S. PATENT DOCUMENTS 5,394,489 A * 2/1995 Koch ................. G02B 6/12004
257/E27.128
6,091,753 A * 7/2000 Capasso ................. B82Y 20/00
372/44.01
(Continued)

OTHER PUBLICATIONS

Author: Seungyong Jung et al., Title: Recent Progress in Widely Tunable Single-Mode Room Temperature Terahertz Quantum Cascade Laser Sources, Date: Nov. 2015, Publisher: IEEE.*
(Continued)

*Primary Examiner* — Taeho Jo
(74) *Attorney, Agent, or Firm* — Bell & Manning, LLC

(57) ABSTRACT

Monolithic, wavelength-tunable QCL devices are provided which comprise a substrate, an array of QCLs formed on the substrate and an optical beam combiner formed on the substrate electrically isolated from the array of QCLs. In embodiments, the QCL devices are configured to provide laser emission in the range of from about 3 μm to about 12 μm, a wavelength tuning range of at least about 500 cm$^{-1}$, and a wavelength tuning step size of about 1.0 nm or less.

13 Claims, 21 Drawing Sheets

(51) Int. Cl.

| | |
|---|---|
| *G01N 21/3504* | (2014.01) |
| *G01N 21/39* | (2006.01) |
| *H01S 5/028* | (2006.01) |
| *H01S 5/10* | (2006.01) |
| *H01S 5/34* | (2006.01) |
| *H01S 5/343* | (2006.01) |
| *G02B 6/00* | (2006.01) |
| *H01S 5/0625* | (2006.01) |
| *G01N 21/35* | (2014.01) |
| *H01S 5/12* | (2006.01) |
| *H01S 5/40* | (2006.01) |
| *H01S 5/026* | (2006.01) |
| *H01S 5/22* | (2006.01) |
| *H01S 5/02* | (2006.01) |

(56) References Cited

U.S. PATENT DOCUMENTS

| | | | |
|---|---|---|---|
| 6,195,381 B1 | 2/2001 | Botez et al. | |
| 6,560,259 B1* | 5/2003 | Hwang | B82Y 20/00 372/102 |
| 7,224,041 B1* | 5/2007 | Sherohman | H01L 21/02398 257/190 |
| 7,295,366 B2* | 11/2007 | Tanaka | H01S 5/026 359/344 |
| 7,386,024 B2* | 6/2008 | Sekiguchi | B82Y 20/00 372/45.01 |
| 7,403,552 B2* | 7/2008 | Botez | B82Y 20/00 372/43.01 |
| 7,542,503 B2* | 6/2009 | Anselm | H01S 5/12 372/26 |
| 7,856,042 B2* | 12/2010 | Botez | B82Y 20/00 372/43.01 |
| 9,182,272 B2* | 11/2015 | Mochizuki | G01J 1/0204 |
| 2002/0110328 A1 | 8/2002 | Bischel et al. | |
| 2003/0214991 A1* | 11/2003 | Wiedmann | H01S 5/026 372/50.12 |
| 2003/0219052 A1* | 11/2003 | Goodhue | B82Y 20/00 372/45.012 |
| 2003/0219054 A1* | 11/2003 | Capasso | B82Y 20/00 372/50.22 |
| 2004/0095579 A1* | 5/2004 | Bisson | G01N 21/1702 356/432 |
| 2004/0228384 A1 | 11/2004 | Oh et al. | |
| 2007/0172169 A1* | 7/2007 | Kish, Jr. | B82Y 20/00 385/14 |
| 2007/0216996 A1* | 9/2007 | Tanaka | H01S 5/026 359/344 |
| 2007/0248131 A1* | 10/2007 | Botez | B82Y 20/00 372/43.01 |
| 2008/0310470 A1* | 12/2008 | Ooi | B82Y 20/00 372/44.01 |
| 2009/0022196 A1* | 1/2009 | Botez | B82Y 20/00 372/45.012 |
| 2011/0216794 A1* | 9/2011 | Howard | B82Y 20/00 372/38.01 |
| 2012/0033697 A1* | 2/2012 | Goyal | B82Y 20/00 372/45.01 |
| 2012/0236889 A1* | 9/2012 | Caneau | B82Y 20/00 372/45.01 |
| 2012/0287418 A1 | 11/2012 | Scherer et al. | |
| 2013/0121359 A1* | 5/2013 | Mansour | H01S 5/34 372/45.012 |
| 2014/0185980 A1* | 7/2014 | Lei | G02B 6/12004 385/14 |
| 2014/0355637 A1* | 12/2014 | Hashimoto | H01S 5/3401 372/45.012 |
| 2014/0356001 A1* | 12/2014 | Barton | H04B 10/505 398/183 |
| 2015/0008327 A1* | 1/2015 | Caneau | G01N 21/39 250/341.8 |
| 2015/0110137 A1* | 4/2015 | Zheng | H01S 5/06 372/20 |
| 2015/0244144 A1* | 8/2015 | Yang | H01S 5/0622 372/20 |
| 2015/0263488 A1* | 9/2015 | Caneau | H01S 5/3402 372/20 |
| 2015/0270685 A1* | 9/2015 | Caneau | H01S 5/028 372/20 |
| 2015/0331298 A1* | 11/2015 | Yagi | G02F 1/2255 385/2 |
| 2016/0109655 A1* | 4/2016 | Vurgaftman | G02B 6/122 385/14 |
| 2016/0156153 A1* | 6/2016 | Belkin | H01S 5/1096 372/45.012 |
| 2016/0352072 A1* | 12/2016 | Belkin | H01S 5/1021 |

OTHER PUBLICATIONS

Author: S. Slivken et al., Title: Sampled grating, distributed feedback quantum cascade lasers with broad tunability and continuous operation at room temperature, Date: 2012, Publisher: American Institute of Physics.*

Bandyopadhyay et al., Ultra-broadband quantum cascade laser, tunable over 760 $cm^{-1}$, with balanced gain, Optics Express, vol. 23, No. 16, Aug. 4, 2015, pp. 21159-21164.

Hugi et al., External cavity quantum cascade laser tunable from 7.6 to 11.4 µm, Applied Physics Letters 95, 061103, Aug. 11, 2009.

Ishii et al., Widely Wavelength-Tunable DFB Laser Array Integrated With Funnel Combiner, IEEE Journal of Selected Topics in Quantum Electronics, vol. 13, No. 5, Sep. 2007, pp. 1089-1094.

Kalchmair et al., High tuning stability of sampled grating quantum cascade lasers, Optics Express, vol. 23, No. 12, Jun. 5, 2015, pp. 15734-15747.

Kudo et al., 1.55-µm Wavelength-Selectable Microarray DFB-LD's with Monolithically Integrated MMI Combiner, SOA, and EA-Modulator, IEEE Photonics Technology Letters, vol. 12, No. 3, Mar. 2000, pp. 242-244.

Lyakh et al., External cavity quantum cascade lasers with ultra rapid acousto-optic tuning, Applied Physics Letters 106, 141101, Apr. 6, 2015.

Meng et al., Broadly continuously tunable slot waveguide quantum cascade lasers based on a continuum-to-continuum active region design, Applied Physics Letters 107, 111110, Sep. 18, 2015.

Slivken et al., Sampled grating, distributed feedback quantum cascade lasers with broad tunability and continuous operation at room temperature, Applied Physics Letters 100, 261112, Jun. 29, 2012.

Slivken et al., Dual Section Quantum Cascade Lasers with Wide Electrical Tuning, Proc. of SPIE vol. 8631, 86310P, Feb. 2013.

Razeghi et al., Widely Tunable, Single-Mode, High-Power Quantum Cascade Lasers, Proc. of SPIE vol. 8069, 806905, 2011.

Zhou et al., Monolithically, widely tunable quantum cascade lasers based on a heterogeneous active region design, Scientific Reports, 6: 25213, Jun. 8, 2016.

International Search Report and Written Opinion mailed in PCT Application No. PCT/US2016/059662, dated Jul. 6, 2017.

\* cited by examiner

MONOLITHICAL WIDELY TUNABLE QUANTUM CASCADE LASER DEVICES

CROSS-REFERENCE TO RELATED APPLICATIONS

The present application claims priority to U.S. Provisional Patent Application No. 62/275,351 that was filed Jan. 6, 2016, the entire contents of which are hereby incorporated by reference.

REFERENCE TO GOVERNMENT RIGHTS

This invention was made with government support under HSHQDC-13-C-00034 awarded by the Department of Homeland Security. The government has certain rights in the invention.

BACKGROUND

Many chemicals like $N_2O$, $CH_4$, $CO_2$ have their signature absorption spectra in the mid-infrared (mid-IR) wavelength range. For chemical-sensing based applications, including medical diagnostics, explosive detections and industrial process monitoring, a portable laser emitting in a wide frequency range is desirable. Quantum cascade lasers (QCLs) have been the leading semiconductor laser sources in the mid-IR wavelength range, thanks to the rapid developments in power, wall-plug efficiency, and single mode operation in the last few years. However, the demonstrated frequency tuning either relies on external cavity or has limited wavelength tuning range. Broadband QCLs with heterogeneous active region designs having an extremely broad gain width are useful for mid-IR spectroscopy. Nevertheless, a tunable QCL requires not only a broadband gain medium but also a robust tuning mechanism that allows selecting any wavelength at will in a wide wavelength range.

SUMMARY

Provided are quantum cascade laser (QCL) devices and systems including the devices.

In one aspect, QCL devices are provided. In embodiments, a monolithic, wavelength-tunable QCL device comprises a substrate, an array of QCLs formed on the substrate and an optical beam combiner formed on the substrate electrically isolated from the array of QCLs.

In the array of QCLs, each QCL comprises a first QCL section and a second QCL section electrically isolated from the first QCL section. Each QCL comprises a quantum cascade (QC) core comprising n QC emitters wherein n is an integer of 2 or greater, a grating layer over the QC core, and a cladding layer over the QC core.

Each QC emitter comprises at least one stage comprising a superlattice of quantum well layers and barrier layers defining an active region configured to generate light having a wavelength $\lambda$ under an applied bias voltage. Each QC emitter is configured to generate light having a different wavelength such that the QC core generates light having wavelengths $\lambda_1$ to $\lambda_n$.

The grating layer is configured to provide optical feedback for a selected wavelength of light generated by the QC core and to produce lasing at the selected wavelength of light. The grating layer comprises a first sampled grating distributed feedback grating (SGDFB) section associated with the first QCL section and a second SGDFB section associated with the second QCL section. The first SGDFB grating section comprises grating regions periodically alternating with gratingless regions and characterized by a grating period $\Lambda_g$, a grating number $N_g$, and a first sampling period $Z_1$. The second SGDFB grating section comprises grating regions periodically alternating with gratingless regions and characterized by the grating period $\Lambda_g$, the grating number $N_g$, and a second sampling period $Z_2$. The grating layer of each QCL is characterized by a different grating period $\Lambda_g$.

The optical beam combiner is configured to convey and amplify the laser light produced from each QCL to a single exit aperture. The optical beam combiner comprises a plurality of input waveguide structures, each input waveguide structure optically coupled to an associated QCL; a coupler waveguide structure optically coupled to the plurality of input waveguide structures; and a single output waveguide structure having the single exit aperture from which laser emission exits. Each input waveguide structure, the coupler waveguide structure and the single output waveguide structure comprise the QC core and the cladding layer.

In other aspects, wavelength-tunable systems comprising the QCL devices and sensors comprising the wavelength-tunable systems are provided.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

DETAILED DESCRIPTION

Provided are quantum cascade laser (QCL) devices and systems including the QCL devices. The QCL devices provide a source of wavelength tunable light and, in at least some embodiments, are capable of providing a very wide wavelength tuning range (e.g., greater than 500 $cm^{-1}$) as well as fine control over the wavelength (e.g., wavelength tuning step size of about 0.5 nm). The QCL devices can be formed as monolithic structures, by which it is meant they are formed on a single chip (i.e., substrate). The QCL devices can also provide laser emission from a single exit aperture. These features provide a robust and compact source of wavelength-tunable light without any moving parts. The QCL devices can be incorporated into systems including components for driving and controlling the components of the QCL devices to very rapid scan speeds (e.g., about 1 kHz).

Use of directional terms throughout this disclosure, such as top, bottom, right, left, front, back, above, under, etc. are merely intended to facilitate reference to various surfaces that form components of the devices referenced herein and are not intended to be limiting in any manner.

Figure 1:
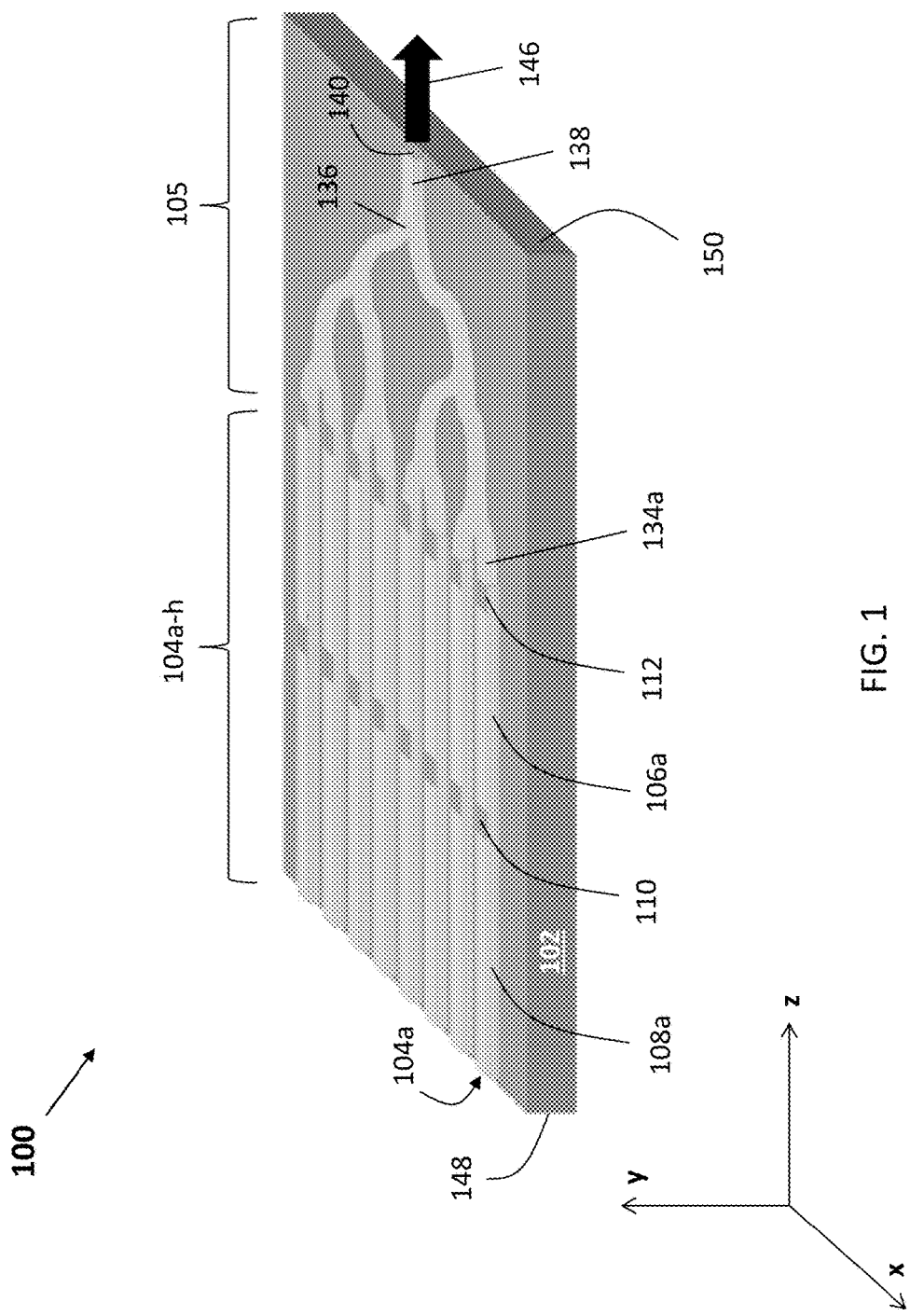
FIG. 1 depicts a perspective view of a quantum cascade laser (QCL) device according to an illustrative embodiment.

In one aspect, a monolithic, wavelength-tunable quantum cascade laser (QCL) device is provided. A perspective view of an illustrative device 100 is shown in FIG. 1. The longitudinal dimension of the device is along axis z and the lateral dimension is along axis x. The device 100 includes a substrate 102, an array of QCLs 104a-h formed on the substrate 102, and an optical beam combiner 105 formed on the same substrate 102.

The array of QCLs includes eight individual QCLs 104a-h. However, various numbers of individual QCLs may be used in the array, e.g., 6, 10, 20, etc. The particular number may be selected depending upon the desired wavelength tuning range of the QCL device and the wavelength tuning range of an individual QCL. As shown in FIG. 1, the multilayer structure from which the QCL device 100 is formed may be processed to form the individual QCLs 104a-h as ridges (e.g., about 5-15 μm wide across the z axis) extending parallel to one another and longitudinally across the substrate 102. Gaps separate adjacent QCLs in the lateral direction. Using QCL 104a as an example, each individual QCL 104a-h is composed of a front QCL section 106a and a back QCL section 108a, which is electrically isolated from the front QCL section 106a via a channel 110 defined in the multilayer structure. Another channel 112 electrically isolates the optical beam combiner 105 from the array of QCLs 104a-h. Although the embodiment shown in FIG. 1 uses two QCL sections, additional sections may be used to improve wavelength tuning behavior.

Figure 2A:
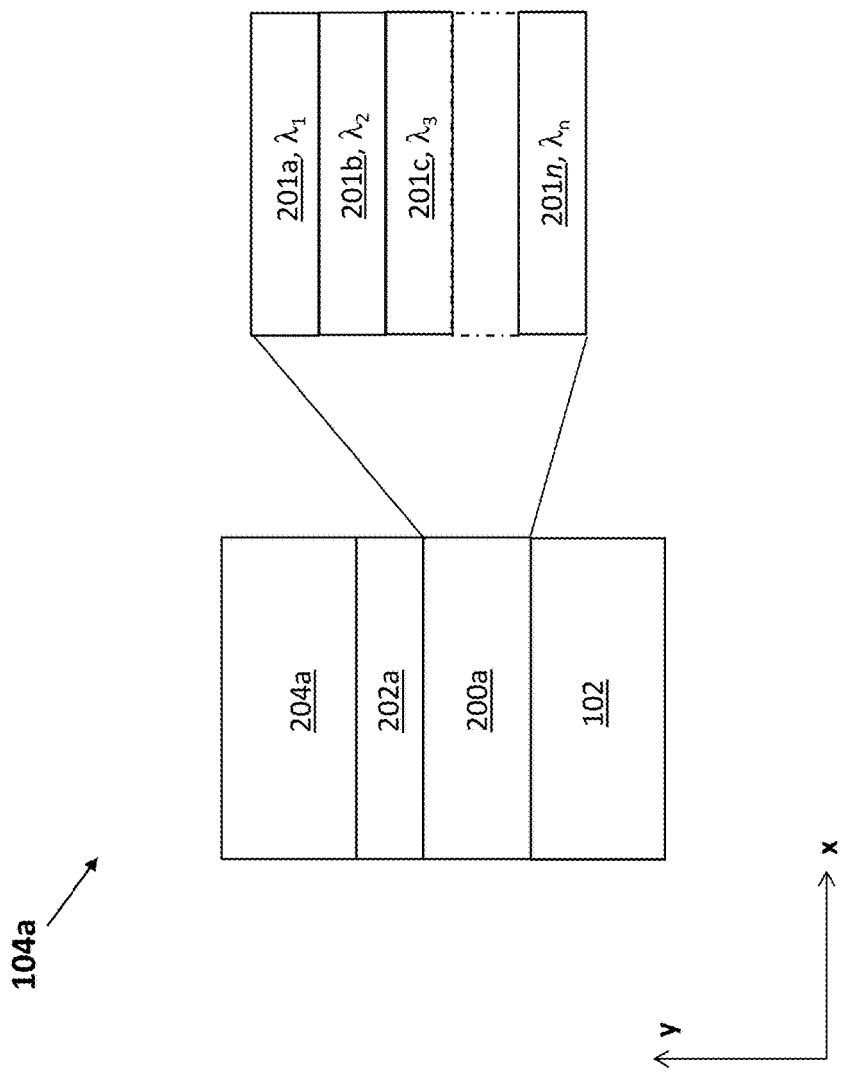
FIG. 2A depicts a cross-sectional view of an individual QCL of the QCL device of FIG. 1.
Figure 2B:
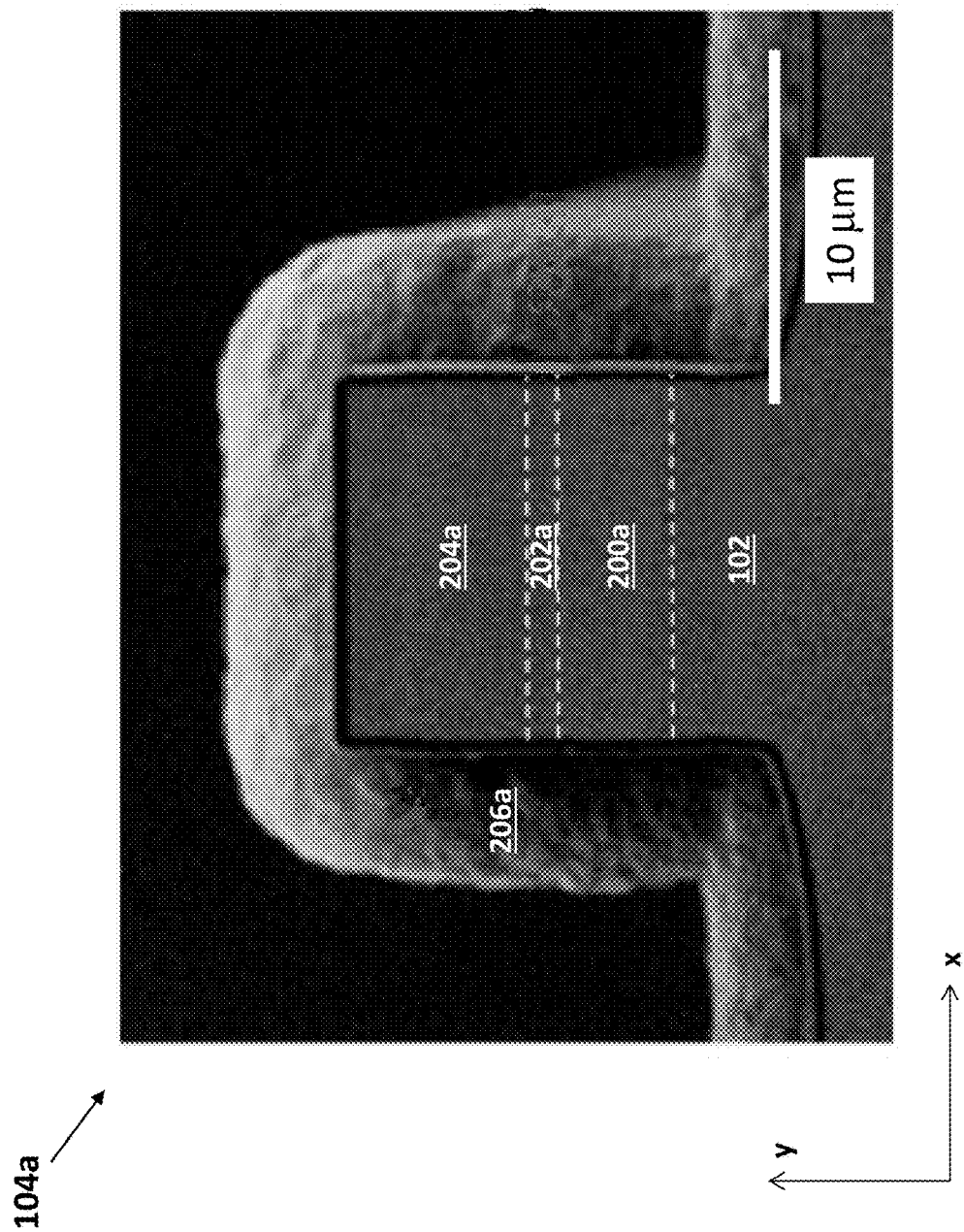
FIG. 2B shows a scanning electron microscope (SEM) image of a cross-section of an individual QCL of the QCL device of FIG. 1.
Figure 2C:
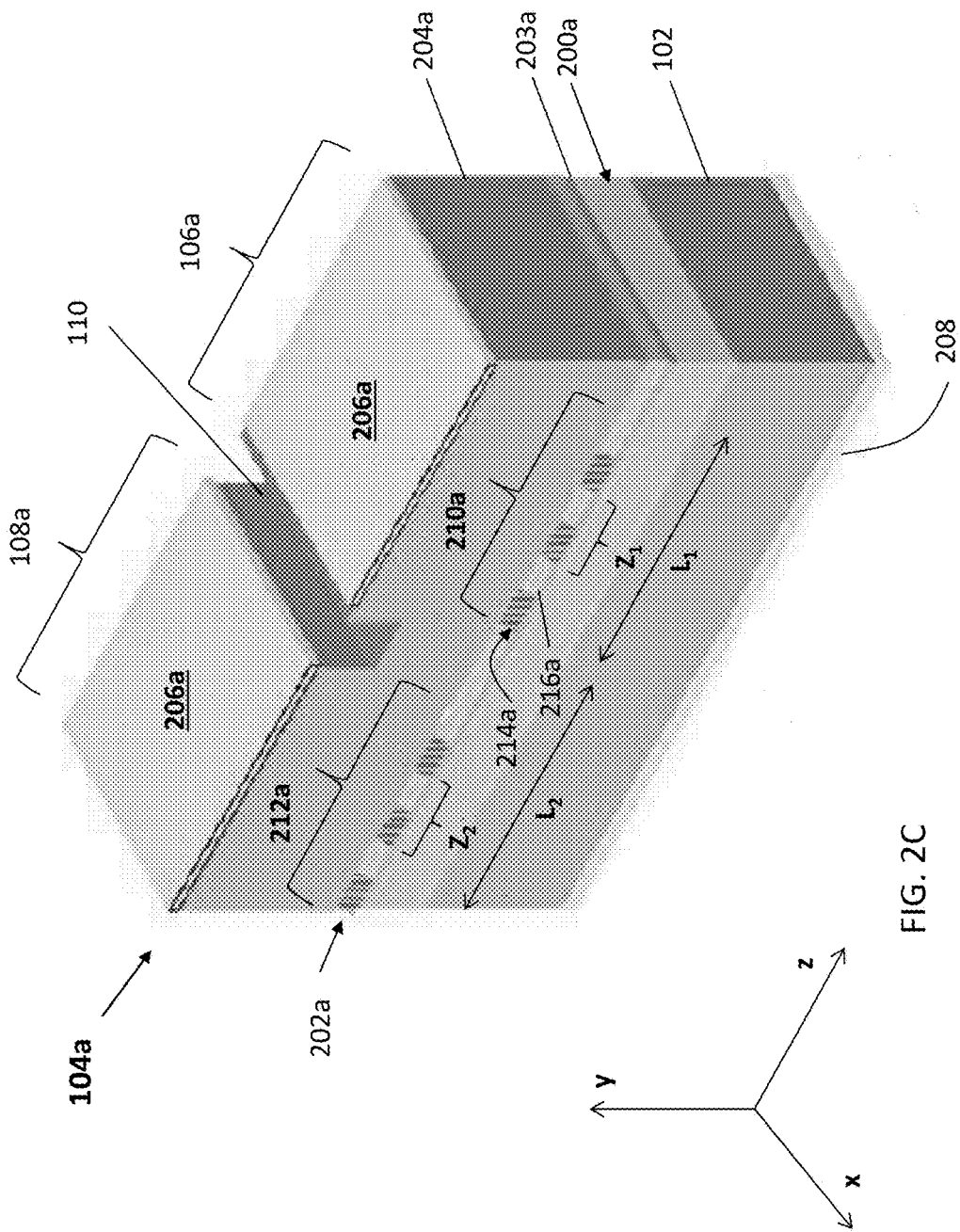
FIG. 2C depicts a perspective view of an individual QCL of the QCL device of FIG. 1.

FIG. 2A shows a cross-sectional view of QCL 104a formed on the substrate 102 taken along the xy plane, illustrating the multilayer structure. FIG. 2B shows a back facet view of another embodiment of QCL 104a, formed according to the methods described in the Example, below. FIG. 2C shows a perspective view of QCL 104a. The QCL 104a includes a quantum cascade (QC) core 200a over the substrate 102, a grating layer 202a over the QC core 200a, and a cladding layer 204a over the QC core 200a. Other material layers may be included in the multilayer structure, e.g., a buffer layer between the QC core 200a and the substrate 102; a spacer layer 203a between the QC core 200a and the grating layer 202a; a cap layer over the cladding layer 204a; a top contact layer 206a; a bottom contact layer 208; confinement layers above (and below) the QC core 200a, etc. Also shown in FIG. 2C is a portion of the channel 110 extending partially (e.g., about 1-5 μm deep) into the cladding layer 204a (and any cap layer thereon).

Figure 4A:
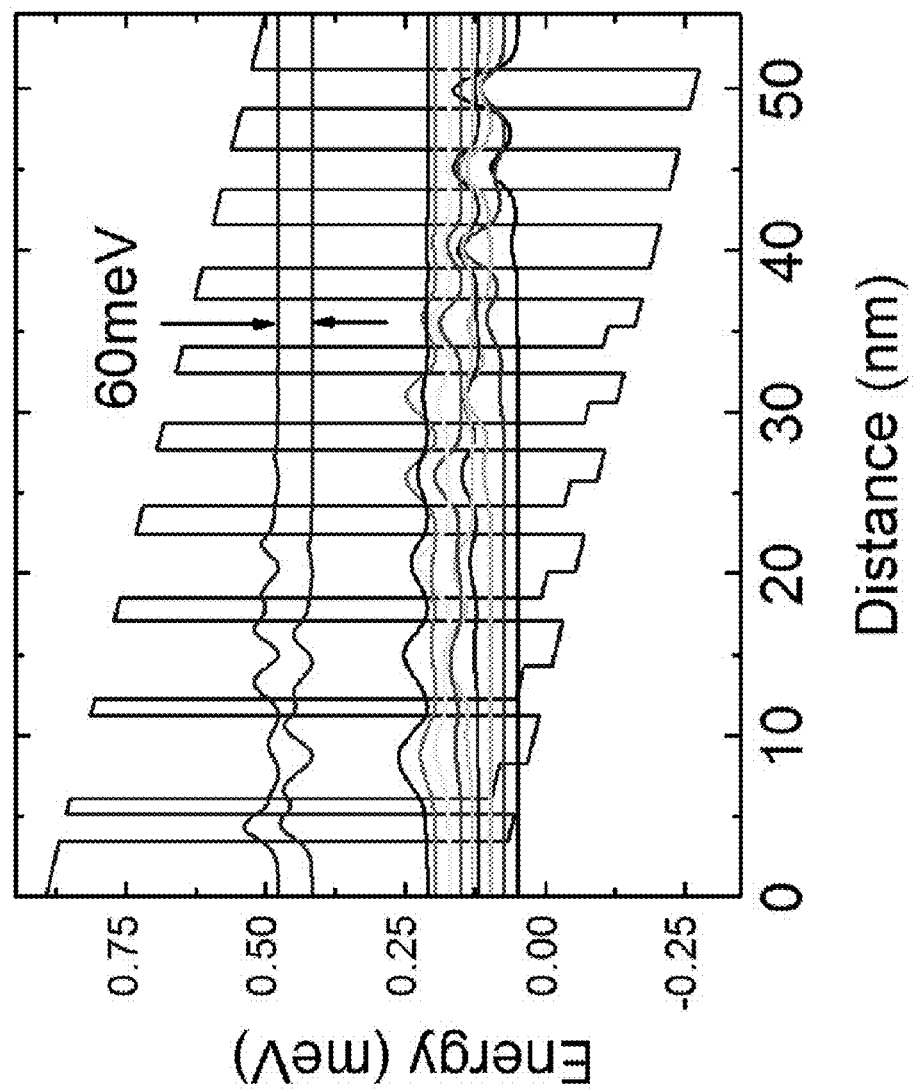
FIG. 4A illustrates the wavefunctions of a quantum cascade (QC) emitter based on an $Al_{0.63}In_{0.37}As/$ $Ga_{0.35}In_{0.65}As/Ga_{0.47}In_{0.53}As$ material system used in the individual QCLs of the QCL device of FIG. 1.

As shown in the inset of FIG. 2A, the QC core 200a is itself another multilayer structure including a plurality of QC emitters 201a-n, wherein n is an integer of 2 or greater, each QC emitter including at least one stage including a superlattice of quantum well layers and barrier layers. Each stage includes an active region configured to generate light having a wavelength $\lambda_1$ when the QCL 104a is under an applied bias voltage. FIG. 4A shows a conduction-band diagram under an applied bias voltage of an illustrative stage including an active region configured to generate light having a wavelength $\lambda_1$. The active region of FIG. 4A is based on intersubband transitions between one upper energy state, primarily aligned with the ground state in the lower miniband of an injector region of the stage, and a miniband in the lower part of the active region. Each QC emitter of the QC core 200a is configured to generate light having a different wavelength, e.g., $\lambda_1, \lambda_2 \ldots \lambda_n$, for n QC emitters. Band engineering is used (i.e., selection of the composition, thicknesses, and arrangement of the quantum well layers and barrier layers in the stages of the QC emitters) to provide the desired mechanism of light generation, wavelength and bandwidth. Each QC emitter may include various numbers of stages, e.g., 8, 10, 12, 24, etc. The number (e.g., 2, 5, 6, 10, etc.) and arrangement (e.g., symmetric, nonsymmetrical) of the QC emitters in the QC core 200a is optimized to realize a constant modal gain and threshold current over the desired wavelength tuning range for the QCL 104a (see, e.g., FIGS. 4B (total modal gain) and 4C (threshold current) for a QC core including 5 QC emitters). Further discussion of the optimization of QC cores based on pluralities of QC emitters may be found in Bandyopadhyay, N., et al., *Optics Express* 21159, Vol. 23, No. 16, Aug. 10, 2015, which is hereby incorporated by reference in its entirety.

As noted above, the QCL 104a includes a grating layer 202a configured to provide optical feedback for a selected wavelength of light generated by the QC core 200a and to produce lasing at the selected wavelength of light. As shown in FIG. 2C, the grating layer 202a includes a front sampled grating distributed feedback (SGDFB) section 210a associated with the front QCL section 106a. The front SGDFB section 210a includes grating regions (one of which is labeled 214a) which periodically alternate in a longitudinal direction across the QCL device 100 with gratingless regions (one of which is labeled 216a). Each grating region of the front SGDFB section 204a includes grating elements which also periodically alternate in a longitudinal direction across the QCL device 100, wherein adjacent grating elements have different indices of refraction (e.g., by being composed of two different semiconductor compounds). The front SGDFB section 210a is characterized by a grating period $\Lambda_g$, a grating number $N_g$, and a first sampling period $Z_1$. The grating period $\Lambda_g = m\lambda/(2n_{eff})$, where m is the grating order, $\lambda$ is the selected wavelength of light generated by the QC core 200a and $n_{eff}$ is the effective index of refraction of the region for $\lambda$. The grating order m is an integer, the value of which may be selected based on the strength of the optical feedback desired and the lithographic capabilities of the fabricator used to form the device. The value of $N_g\Lambda_g$ is the length of each grating region; the value of $L_1$ is the total sampled grating length; the value of $N_g\Lambda_g/Z_1$ is the grating duty cycle. Each of these parameters may be selected to optimize the wavelength tuning range, the wavelength tuning step size, and the magnitude of the reflectivity of the light from QCL 104a.

The grating layer 202a also includes a back SGDFB section 212a associated with the back QCL section 108a. The back SGDFB section 212a is configured as described above for the front SGDFB section 210a except that the back SGDFB section 212a is characterized by a different sampling period. In other words, the back SGDFB section 212a is characterized by the grating period $\Lambda_g$, the grating number $N_g$, a second sampling period $Z_2$ and a length $L_2$. Use of two different sampling periods within an individual QCL provides an additional periodicity in the reflectivity spectrum. A greater range of wavelength tuning is possible via the Vernier effect by adjusting the current applied to the electrically isolated front and back QCL sections 106a, 108a. Further discussion of sampled grating distributed feedback lasers may be found in Slivken, S. et al. *Proc. SPIE* 8631, 86310P (2013) and Slivken, S., et al. *Applied Physics Letters* 100, 261112 (2012), each of which is hereby incorporated by reference in its entirety.

As shown in FIGS. 2A-C, the grating layer 202a is a buried grating layer, i.e., it is embedded within the multilayer structure from which the QCL 104a is formed. However, surface grating layers may also be used, e.g., a grating layer disposed on the top surface of the cladding layer 204a. By way of illustration, a surface grating can be used if the grating coupling strength is high enough for wavelength selection. See Lu, Q.Y. et al. *Appl. Phys. Lett.* 98 181106 (2011), which is hereby incorporated by reference in its entirety.

With reference back to the QCL device 100 of FIG. 1, each of the remaining individual QCLs 104b-h are configured as described above for QCL 104a except that each individual QCL 104b-h is characterized by a different grating period, e.g., $\Lambda_{g2}$, $\Lambda_{g3}$ ... $\Lambda_{gn}$, for n QCLs. The step size between the different values of the grating periods depends, at least in part, upon the number of QCLs in the array and the desired wavelength tuning range for the QCL device 100.

With reference back to FIG. 1, the QCL device 100 includes an optical beam combiner 105 formed on the substrate 102. The optical beam combiner 105 is configured to convey and amplify the laser light produced from each individual, separated QCL of the array of QCLs 104a-h to a single exit aperture 140. This may be achieved using various configurations of the optical beam combiner 105. As shown in FIG. 1, the optical beam combiner 105 includes a plurality of input waveguide structures 134a-h (one of which is labeled 134a in FIG. 1; also see 134a-h in FIG. 3A), a coupler waveguide structure 136 and a single output waveguide structure 138. Each input waveguide structure extends from, and is optically coupled to, an end of an associated individual QCL. The coupler waveguide structure 136 is optically coupled to ends of the plurality of input waveguide structures 134a-h and an end of the single output waveguide structure 138. The single output waveguide structure 138 has the single exit aperture 140 at its opposing end from which laser emission 146 exits the QCL device 100. The multilayer structure from which the QCL device 100 is formed may be processed to form the components of the optical beam combiner 105 as ridges (waveguide structures) and slabs (coupler waveguide structures) which both generally extend longitudinally across the substrate 102.

Figure 3A:
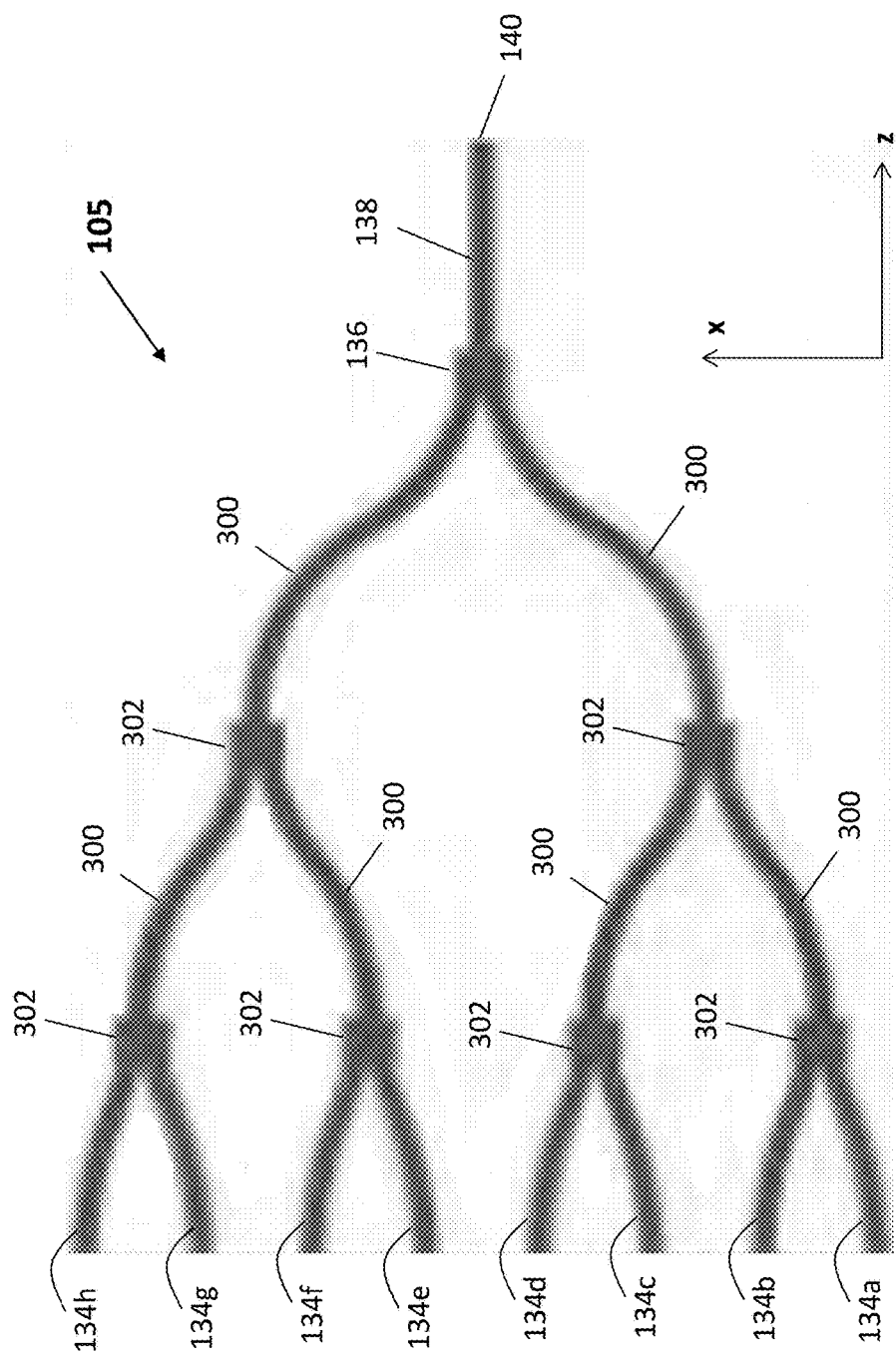
FIG. 3A depicts a top view of an optical beam combiner of the QCL device of FIG. 1.
Figure 3B:
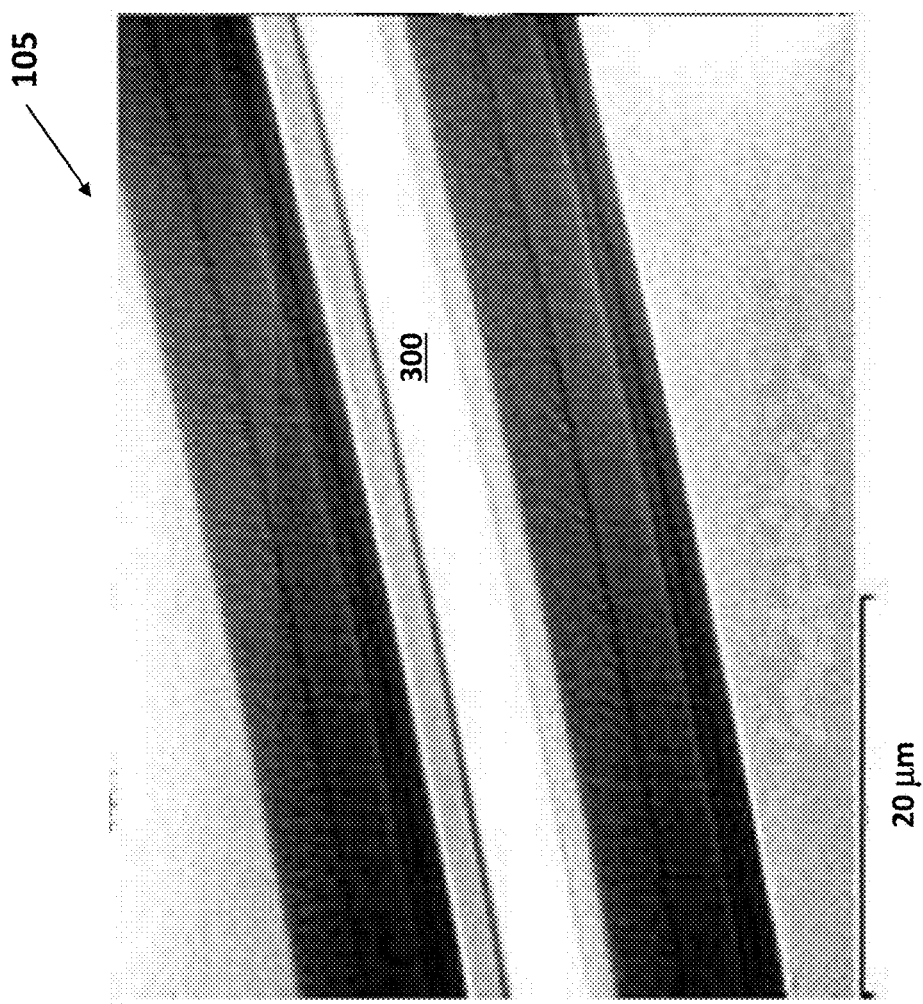
FIG. 3B shows a SEM image of a portion (an intermediate waveguide structure) of an embodiment of the optical beam combiner of FIG. 3A.
Figure 3C:
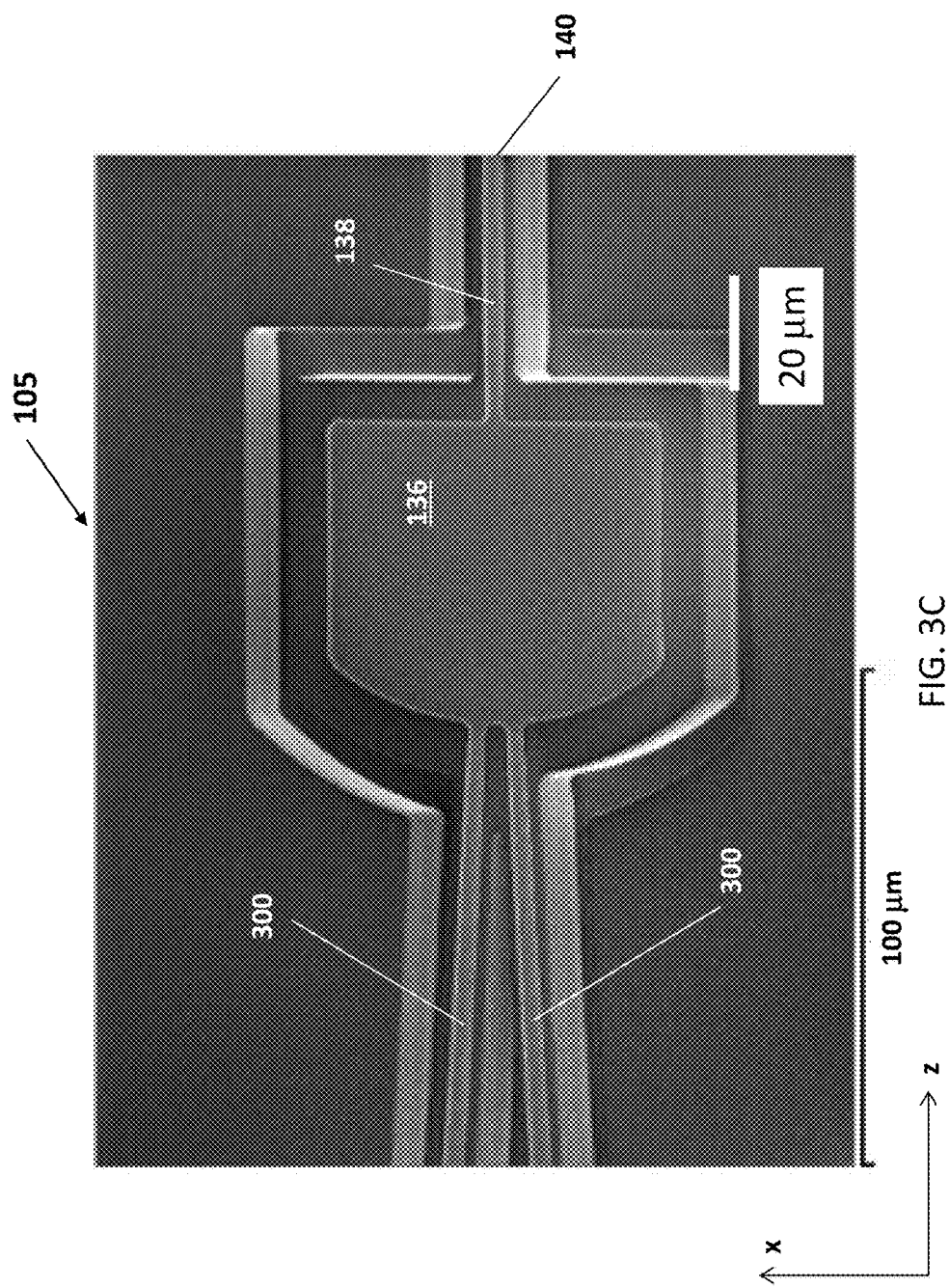
FIG. 3C shows a SEM image of a portion (a coupler waveguide structure) of an embodiment of the optical beam combiner of FIG. 3A. The $Si_3N_4$ passivation and openings on top of the structure are shown.
Figure 3D:
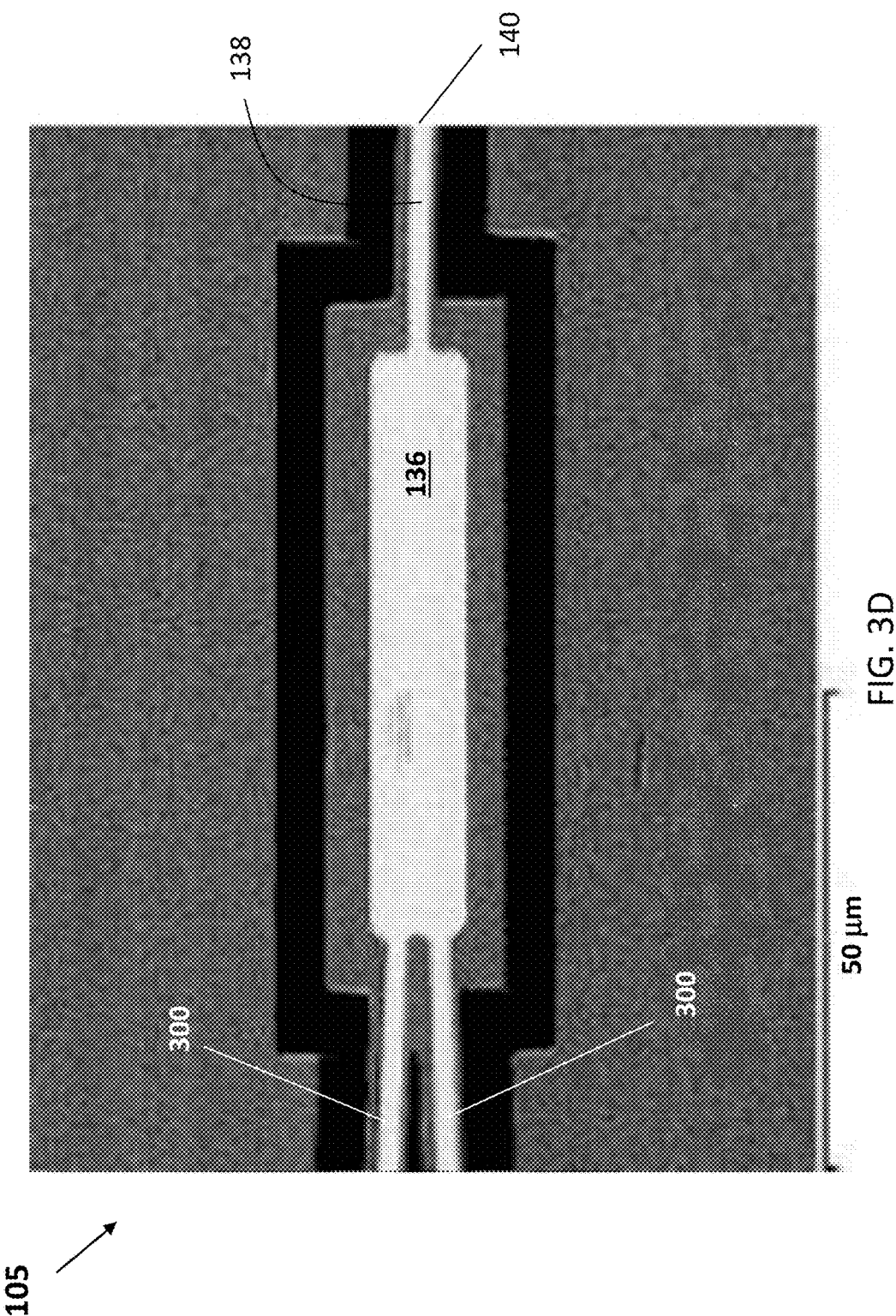
FIG. 3D shows a SEM image of a portion (a coupler waveguide structure) of another embodiment of the optical beam combiner of FIG. 3A.

Various configurations of the optical beam combiner 105 and its components may be used. FIG. 3A shows a top view of the optical beam combiner 105 of FIG. 1. FIG. 3A illustrates that the optical beam combiner 105 may be configured as a "tree-array combiner" in which the plurality of input waveguide structures 134a-h are indirectly coupled to the coupler waveguide structure 136 via a plurality of intermediate waveguide structures 300 and intermediate coupler waveguide structures 302. In this embodiment, the plurality of input waveguide structures 134a-h and the intermediate waveguide structures 300 are curved, S-bend waveguide structures. The coupler waveguide structure 136 and the intermediate coupler waveguide structures 302 are slab waveguides. FIGS. 3B-3D show scanning electron microscope (SEM) images of portions of the optical beam combiner 105 configured as a tree-array combiner and formed according to the methods described in the Example, below. These figures show an S-bend input/intermediate waveguide structure (e.g., 300) (FIG. 3B) and a coupler (intermediate) waveguide structure (e.g., 136) (FIGS. 3C, 3D).

Figure 3E:
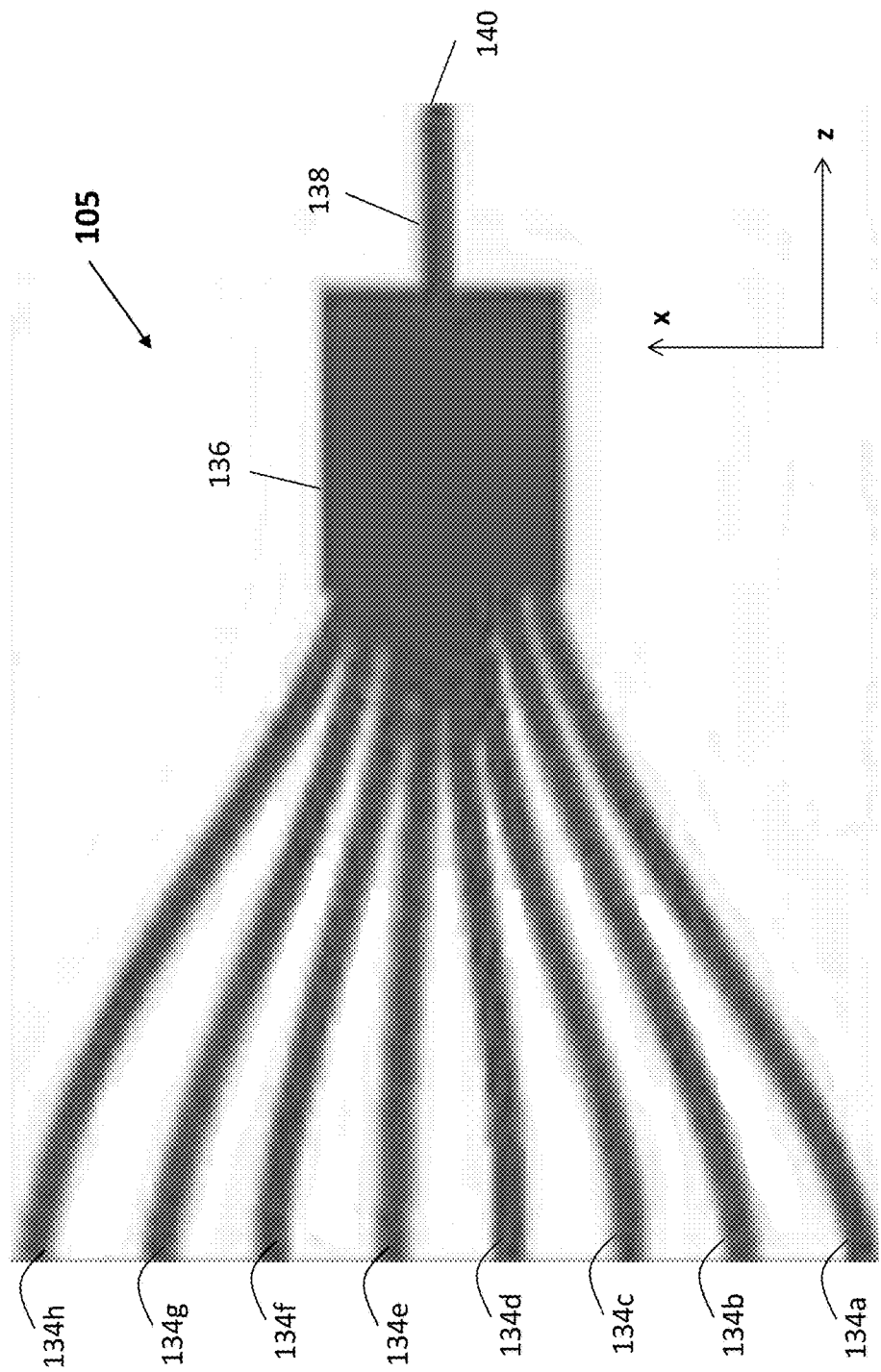
FIG. 3E depicts a top view of another embodiment of the optical beam combiner of the QCL device of FIG. 1.
Figure 3F:
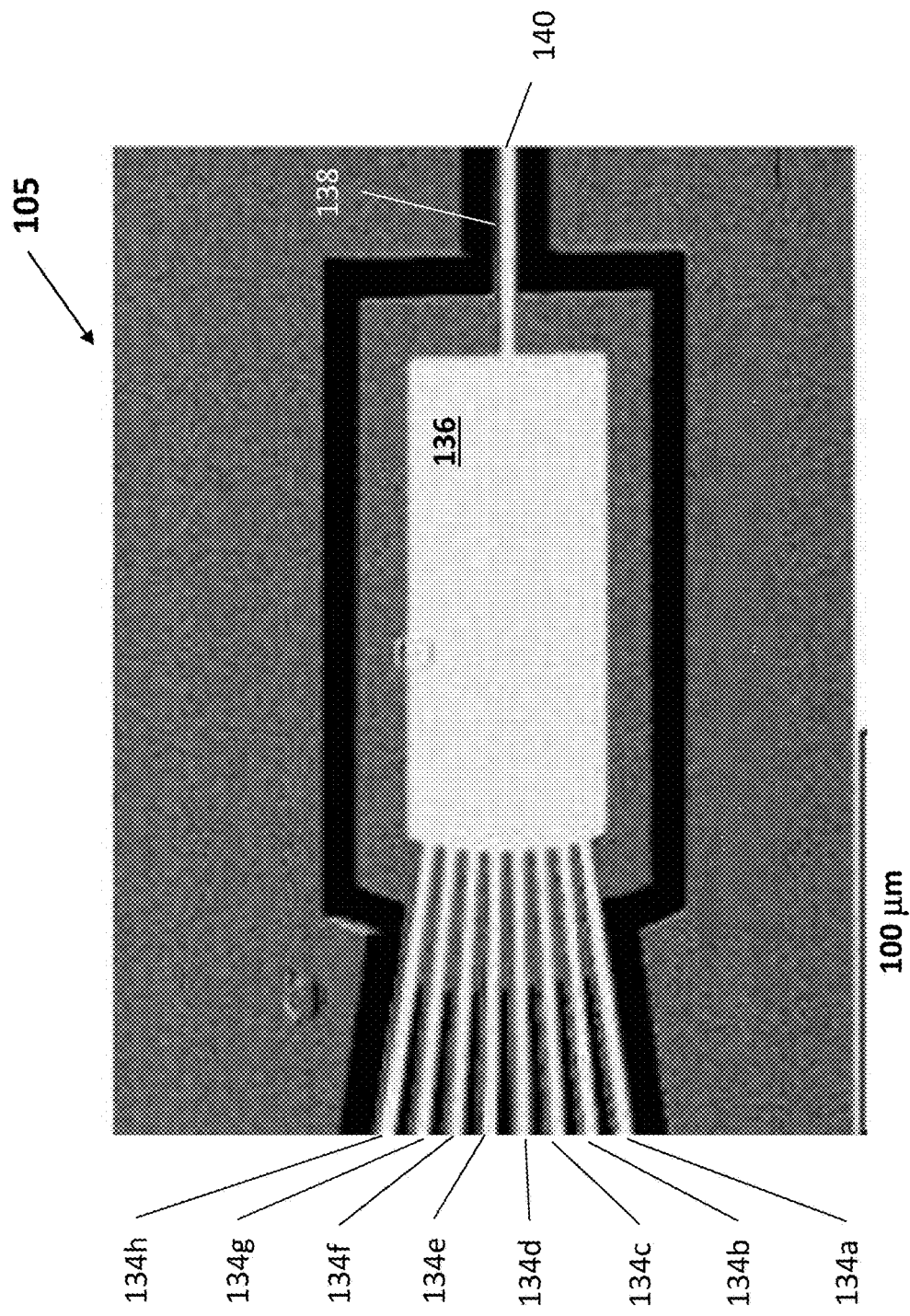
FIG. 3F shows a SEM image of a portion (a coupler waveguide structure) of an embodiment of the optical beam combiner of FIG. 3E.

Another illustrative configuration for the optical beam combiner 105 is shown in FIG. 3E (top view) configured as an "n×1 funnel combiner" in which the plurality of input waveguide structures 134a-h (n=8) are directly optically coupled to the coupler waveguide structure 136. The plurality of input waveguide structures 134a-h are also curved, S-bend waveguide structures and the coupler waveguide structure 136 is a slab waveguide. FIG. 3F shows a SEM image of a portion of the optical beam combiner 105 configured as an 8×1 funnel combiner and formed according to the methods described in the Example, below.

Figure 3G:
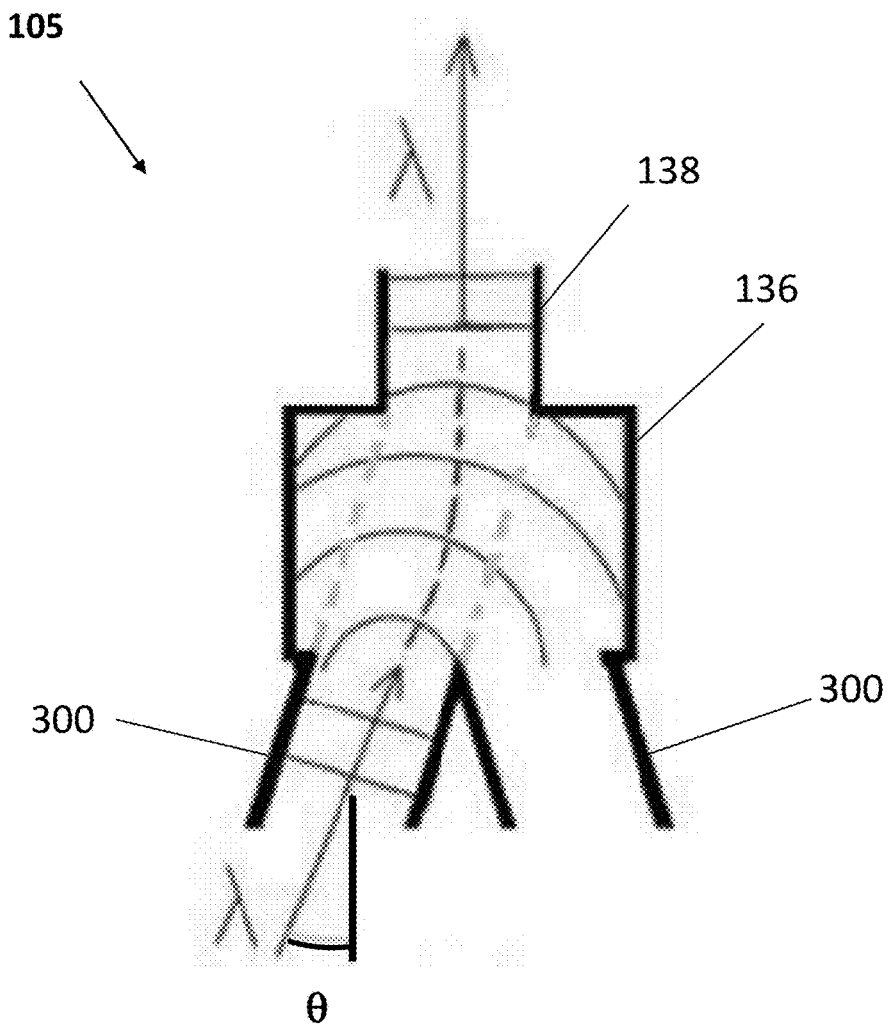
FIG. 3G shows a schematic of the coupler waveguide structure of the optical beam combiner of FIG. 3A to illustrate an insertion angle $\theta$.

In both embodiments, various structural parameters such as the longitudinal dimensions (along the z axis) of the coupler (intermediate) waveguide structures (e.g., about 70-150 µm), the lateral dimension (along the x axis) of the input/intermediate waveguide structures (e.g., about 5-15 µm) and the insertion angle θ (e.g., about 2-10°) of the input/intermediate waveguide structures may be selected to optimize the optical characteristics of the laser emission 146 exiting the single exit aperture 140 (e.g., transmission, reduction of parasitic reflections, preservation of the fundamental transverse mode, Gaussian, single-lobe far-field beam shape, etc.). The insertion angle θ is defined in FIG. 3G, showing a portion of the optical beam combiner 105, including two intermediate waveguide structures 300 optically coupled the coupler waveguide structure 136. This figure shows an insertion angle θ of about 5°; FIG. 3D shows an insertion angle of about 2.5°.

Figure 3H:
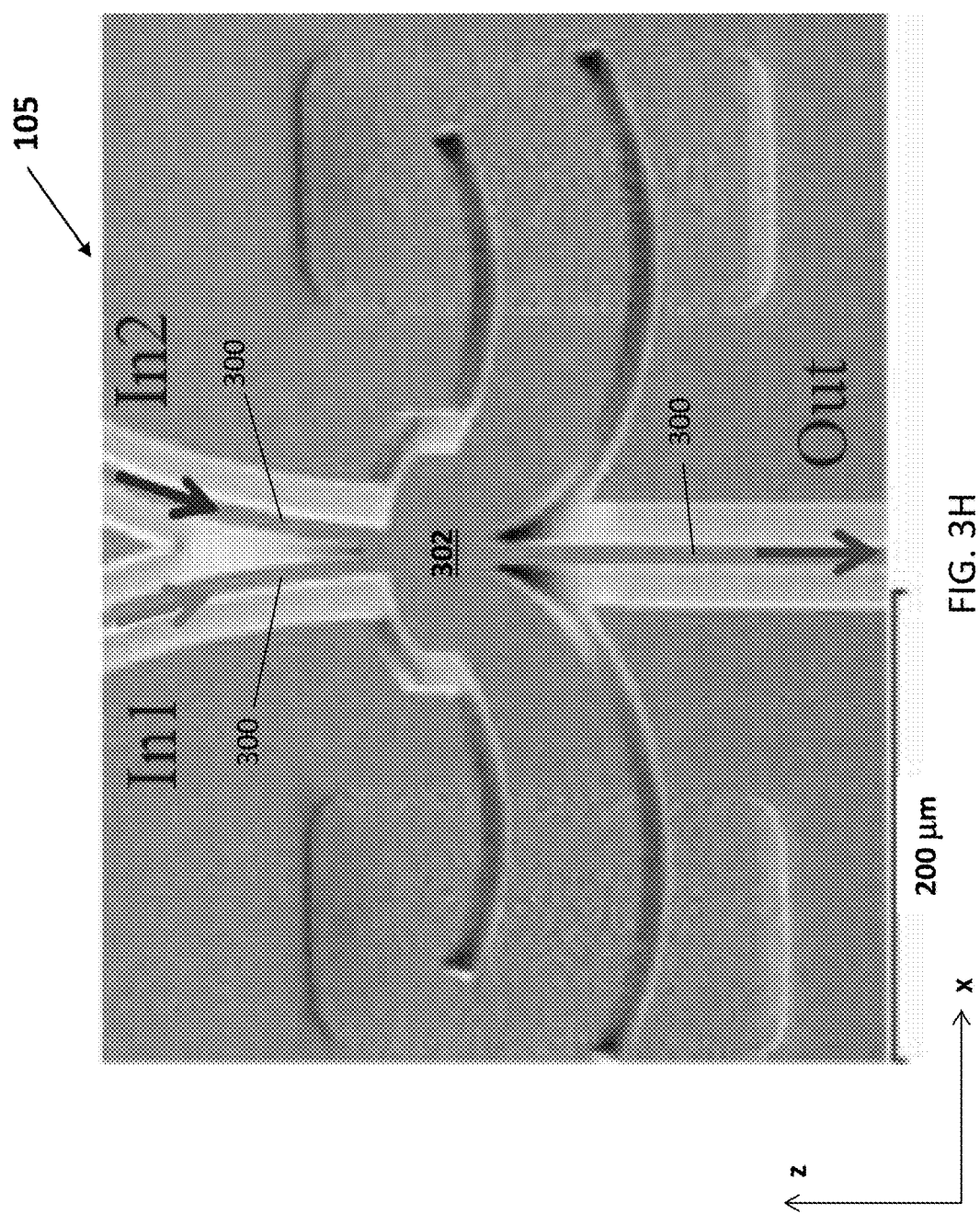
FIG. 3H shows a SEM image of a portion (an intermediate waveguide structure) of an embodiment of the optical beam combiner of FIG. 3A.

Other configurations may be used for the coupler waveguide structure 136 and the intermediate coupler waveguide structures 302. One such embodiment of one of the intermediate coupler waveguide structures 302 is shown in FIG. 3H. This type of winged structure may be useful to reduce parasitic reflections.

As noted above, the optical beam combiner 105 may also be formed from the multilayer structure from which the QCL device 100 is formed. Specifically, the optical beam combiner 105 and the individual QCLs 104a-h may all be formed on the same wafer, with the same layer sequence. This makes the waveguide perfectly continuous. The grating layer 202a may be left intact or removed prior to deposition of the cladding layer 204a. In embodiments, the optical beam combiner 105 includes the QC core material (see FIG. 2A, QC core 200a) and the cladding layer (see FIG. 2A, cladding layer 204a) of the QCL device 100.

Various materials may be used for the multilayer structure from which the QCL device 100 is formed, e.g., group III-V semiconductor compounds. Selection of the particular materials is driven, at least in part, by the band engineering considerations described above. By way of illustration, the substrate 102 may be composed of InP. The QC emitters of the QC core 200a may be composed of AlInAs/GaInAs heterostructures. As is known in the field, the relative amounts of the elements in such semiconductor compounds may vary, i.e., "GaInAs" encompasses those compositions $Ga_{1-x}In_xAs$, wherein x varies from about 0 to about 1. InP may be used for the buffer, spacer, cladding and cap layers. Material layers may be doped to various doping levels, depending upon the function of the material layer. Crystal growth methods such as molecular beam epitaxy (MBE) and metal-organic chemical vapor deposition (MOCVD) may be used to deposit semiconductor layers. Thicknesses of the material layers may be optimized as determined by band engineering considerations and the particular function of the material layer. Methods such as e-beam lithography and dry etching, followed by re-growth, may be used to form the grating layer 202a. Etching may also be used to form the channels 110, 112.

Patterning of the multilayer structure to form the individual QCLs, the input/output waveguide structures and the coupler waveguide structures may be accomplished by plasma etching. With reference to FIG. 1, the multilayer structure may then be cleaved to define a back facet 148 at the back of the QCL device 100 and a front facet 150 at the front of the QCL device 100. The cleaved QCL device 100 may have a length (along the z axis) in the range of, e.g., from about 2 mm to about 1.5 cm. The width (along the x axis) of the QCL device 100 may be in the range of, e.g., from about 1 mm to about 1 cm.

Antireflective (AR) coatings may be formed on the front and/or back facets 150, 148 of the QCL device 100. Various broadband, anti-reflective materials may be used, e.g., $Y_2O_3$. Multilayer coatings may be used, e.g., a first layer of ZnSe and a second layer of $BaF_2$. The materials and thicknesses may be selected to optimize the suppression of undesired emission. Ion-beam sputtering may be used to deposit AR coatings.

Various conductive materials, e.g., metals or metal alloys such as Ti, Au, AuGe, etc., may be used for the top and bottom contact layers (e.g., 206a, 208) on QCL device 100. Methods such as evaporation and electroplating may be used to deposit conductive materials.

Additional details, including specific, illustrative compositions and thicknesses for the multiple layers of the QCL device 100 are provided in the Example, below.

The wavelengths of light generated by the present QCL devices will generally be in the mid-IR range, e.g., from about 3 μm to about 12 μm. This includes embodiments in which the wavelengths of light are in the range of from about 6 μm to about 10 μm. The QCL devices may be characterized by a wavelength tuning range. In embodiments, the wavelength tuning range is at least about 500 $cm^{-1}$. This includes embodiments in which the wavelength tuning range is at least about 550 $cm^{-1}$ or at least about 600 $cm^{-1}$. However, QCL devices configured to provide narrower wavelength tuning ranges may be used, depending upon the desired application. The QCL devices may be characterized by a wavelength tuning step size. In embodiments, the wavelength tuning step size is less than about 1.0 nm. This includes embodiments in which the wavelength tuning step size is less than about 0.5 nm or less than about 0.25 nm. However, QCL devices configured to provide smaller or larger tuning step sizes may be used, depending upon the desired application.

As part of a system for providing wavelength-tunable light, the QCL device 100 may be operably coupled to a variety of electrical components and a controller(s) configured to control the application of current to the various portions of the QCL device 100 (i.e., the front and back QCL sections of each individual QCL in the array of QCLs 104a-h and the optical beam combiner 105). These electrical components may include, e.g., drivers, digital-to-analog converters, multiplexors, field effect transistors, field programmable gate arrays, etc. The controller may include various interfaces, computer-readable media, processors, control applications, etc. The system may be characterized by a scan speed, i.e., the speed at which the QCL device 100 can be scanned over its wavelength tuning range. In embodiments, the scan speed supports at least 500 Hz. However, systems configured to provide faster and slower scanning speeds may be used, depending upon the desired application. The system may further include power supplies operably coupled to the QCL device 100 as well as a thermal-electric cooler (TEC) operably coupled to the QCL device 100 for thermal management.

Figure 7:
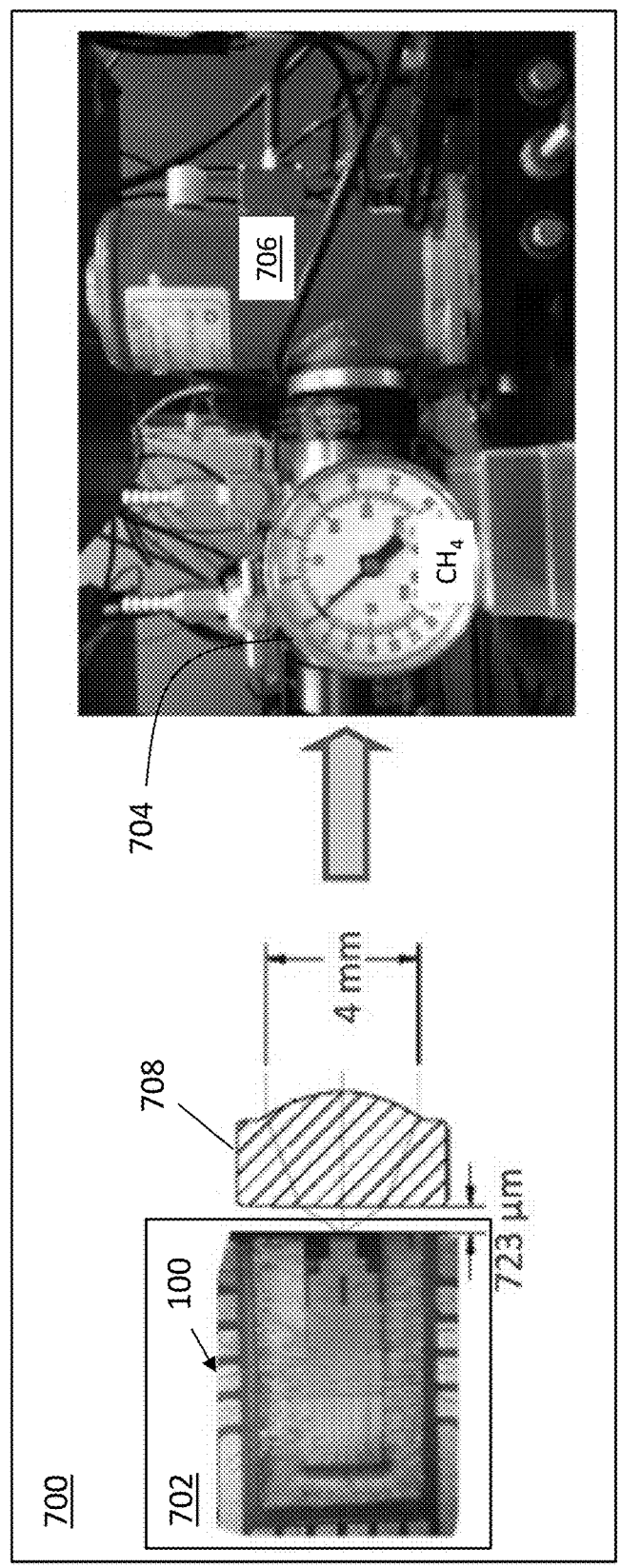
FIG. 7 depicts a sensor including a wavelength-tunable system according to an illustrative embodiment. The wavelength-tunable system (a portion of which is shown) includes the QCL device of FIG. 1, a sample cell mounted to the QCL device and a detector mounted to the sample cell.

The present QCL devices and related systems will find use in a variety of applications, e.g., spectroscopic and chemical sensing applications including medical diagnostics, explosive detection and industrial process monitoring. By way of illustration, an apparatus for spectroscopic identification is described in the Example, below. As depicted in FIG. 7, that apparatus 700 includes a wavelength-tunable system 702 including the QCL device 100. (Only the QCL device 100 is shown.) The apparatus 700 further includes a sample cell 704 configured to accommodate a gas and a detector 706. A black diamond aspheric lens 708 directs the wavelength-tunable laser emission to the sample cell 704, which is a single pass, short path gas cell with KBr windows. The detector 706 is a liquid nitrogen-cooled mercury cadmium telluride (MCT) detector. The QCL device 100 provides a source of the wavelength-tunable light as described above, the sample cell 704 provides the gas to be tested (in this case, $CH_4$), and the detector 706 detects the absorption by components in the gas as a function of wavelength. The components can be identified by their spectroscopic fingerprints.

EXAMPLE

Methods

Growth and fabrication. The QCL device presented in this Example is based on the $Al_{0.63}In_{0.37}As/Ga_{0.35}In_{0.65}As/Ga_{0.47}In_{0.53}As$ material system grown by gas-source molecular beam epitaxy on a semi-insulating InP substrate. The layer sequence and the waveguide doping are as follows: 3-μm InP buffer layer (Si, ~2×10$^{16}$ cm$^{-3}$), five-emitter heterogeneous laser core, 100-nm InP spacer layer (Si, ~2×10$^{16}$ cm$^{-3}$), 750-nm InGaAs grating layer (Si, ~2×10$^{16}$ cm$^{-3}$). The grating is defined with e-beam lithography and dry etching on the InGaAs grating layer. After the grating patterning, a regrowth of 4-μm low-doped cladding (Si, ~2×10$^{16}$ cm$^{-3}$) and 1-μm high-doped cap layer (Si, ~5×10$^{18}$ cm$^{-3}$) is performed by low pressure metalorganic chemical vapor deposition (MOCVD). Two isolation channels were etched. These channels were etched 2.0 μm deep through an 80 μm wide mask into the InP cap and cladding layers. Subsequently, the samples were processed into double channel waveguides with a ridge width of 10 μm by 'Cl$_2$/H$_2$/Ar' plasma etching. Before the formation of top metal contact, a 500 nm thick Si$_3$N$_4$ layer was deposited and etched through on top of the waveguide to define current injection. The top contact is then formed by the evaporation of Ti/Au followed by a lift-off process and the electroplating of a thick gold layer of 3 μm. After polishing the substrate to 150 μm, an AuGe/Ni/Au bottom contact is evaporated. The sample was cleaved into 8.5 mm long bars, and AR coated with 1.3-μm Y$_2$O$_3$ on the beam combiner facet. The device was epi-up mounted on a copper heat sink with indium solder for testing. A perspective view of a schematic of the device is shown in FIG. 1 as described above. A facet view of one of the lasers of the device is shown in FIG. 2B as described above. A top view of the funnel combiner of the beam combiner of the device is shown in FIG. 3C as described above.

Device Testing. All measurements were performed at room temperature. Output mid-IR power in pulsed mode was measured using a calibrated thermopile detector for the average power and the peak power was obtained from the measured average power and the known duty cycle. Spectral measurements were performed with a Bruker Fourier transform infrared (FTIR) spectrometer at a resolution of 0.125 cm$^{-1}$. Due to the high current densities of the devices with epi-up mounting, the lasers had to be operated in pulsed mode (100-ns pulse width, 500-kHz repetition rate), with the addition of DC biases to different sections to tune the laser frequencies. Thus, three independent drivers were used to inject the pulse/DC currents for spectral and power measurements.

Tunable laser system. Within the system, the laser array was mounted on an inverted thermo-electrically cooled (TEC) stage held at a stable heatsink temperature of 15° C. This stage was mounted on invar-alloy posts for maximum laser pointing stability. The lasers within the array shared a common cathode which was grounded to the heatsink. The system used three separate positive polarity laser drivers, each with a variable DC current and pulsed resistively loaded AC voltage. High-efficiency buck-converter power supplies (Texas Instruments TPS54360) with either current or voltage feedback being mixed with a digital to analog converter (DAC) signal were used to dynamically control the DC current and pulsed voltage of each driver. Two 1×8 multiplexors consisting of p-FETs (Vishay Si7309DN) selected the laser array pair to be driver. The pulsed voltage was applied to the selected laser pair and the beam combiner via n-FETs (Vishay SiS892ADN). All of the FETs were driven by an embedded field programmable gate array (FPGA) via isolated gate drivers (Analog Devices ADuM4223). A separate FPGA controlled the DAC settings and monitored the power supplies. The system used an ARM cortex A9 based embedded single board computer (Toradex Colibri T30) as the main controller.

Spectroscopy measurement setup. The spectroscopy measurement setup consisted of the tunable laser system, a gas cell, and a cryogenic mercury cadmium telluride (MCT) detector. (See FIG. 7.) The output from the tunable laser system was sent to the gas cell via a black diamond aspheric lens (~4 mm beam diameter). The gas-cell was filled with methane at 1 atmosphere. The photoconductive detector was biased with 30 mA of DC current though a bias tee, and the output was connected to a high-speed lock-in amplifier (Stanford Research Systems SR488). A 500 kHz synchronization pulse locked to the laser pulsing was used as the reference input to the lock-in amplifier. An external measurement trigger output from the laser system was used to trigger the lock-in amplifier to record a data point into the lock-in's internal storage. The scanning and download of data after a scan were controlled remotely via a custom LabVIEW program. The tunable laser system was scanned between a wavelength range with a designated step size, first with an open beam and then with the methane filled gas cell in the beam path. After correcting for the reflectivity of the windows, these two scan were then divided by each other to reveal the transmission spectrum of the methane.

Results and Discussion

Figure 4B:
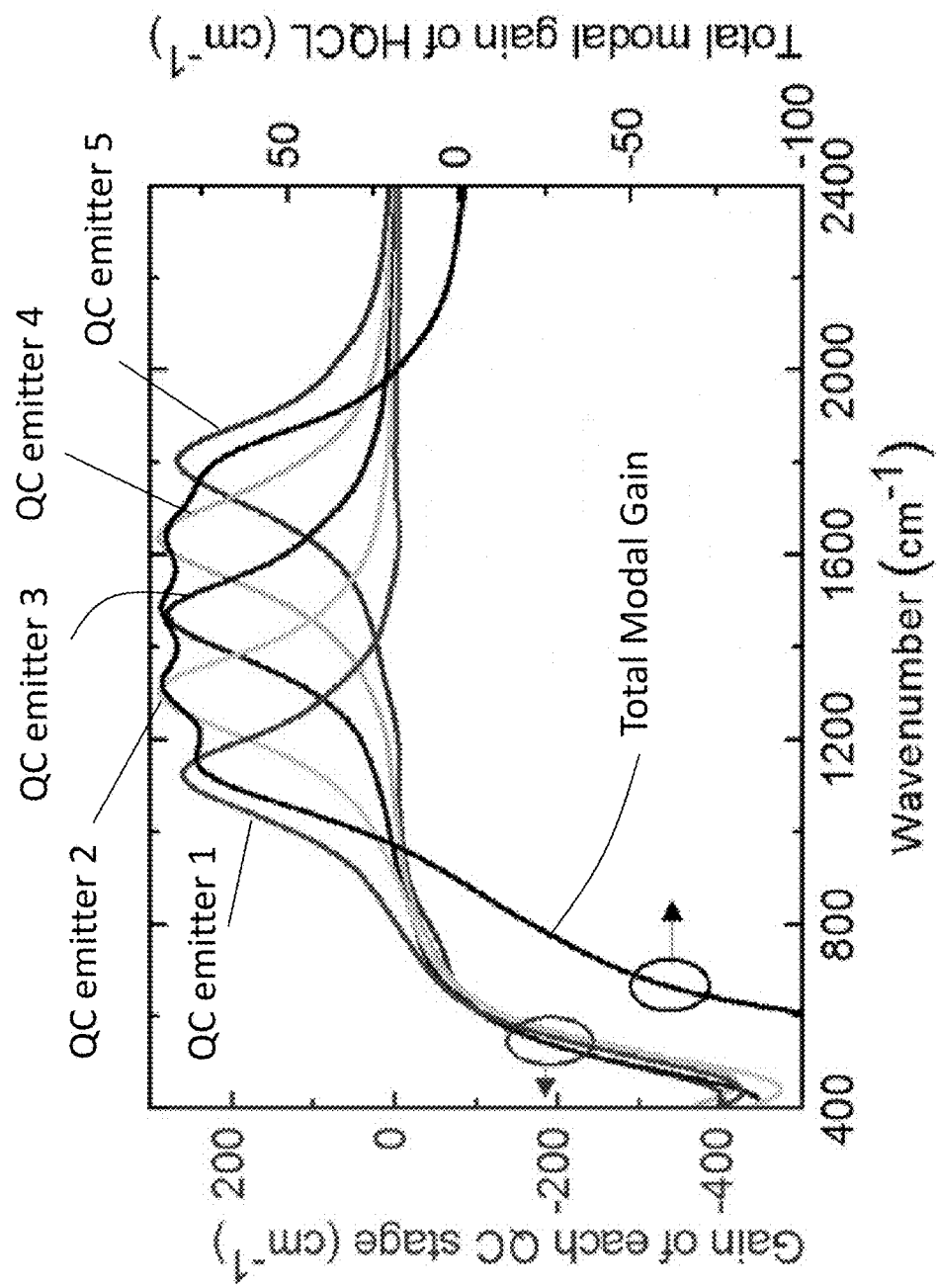
FIG. 4B shows the simulated gain curve of a QC core including five QC emitters for the individual QCLs of the QCL device of FIG. 1.
Figure 4C:
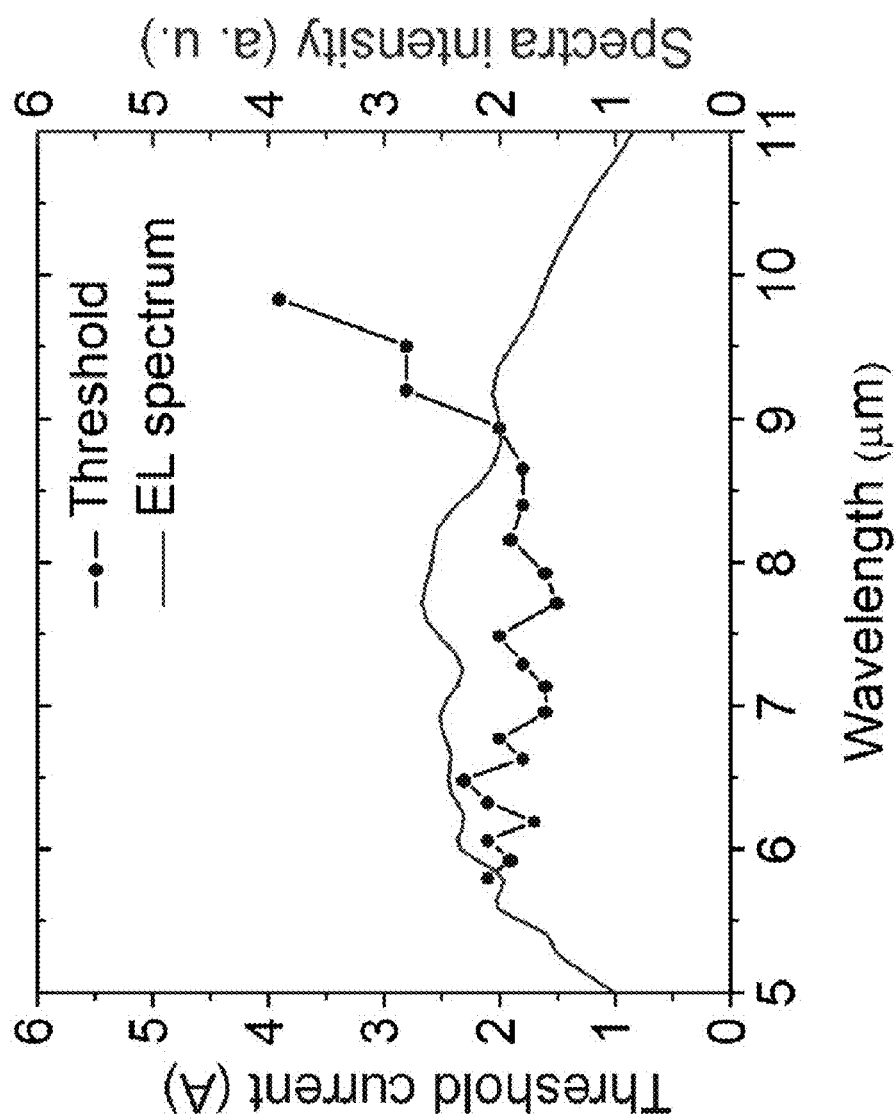
FIG. 4C shows an overlay plot of the electroluminescence (EL) curve, single mode distributed feedback (DFB) array threshold, and multimode emission peak as a function of wavelength for the QC core of FIG. 4B.
Figure 4D:
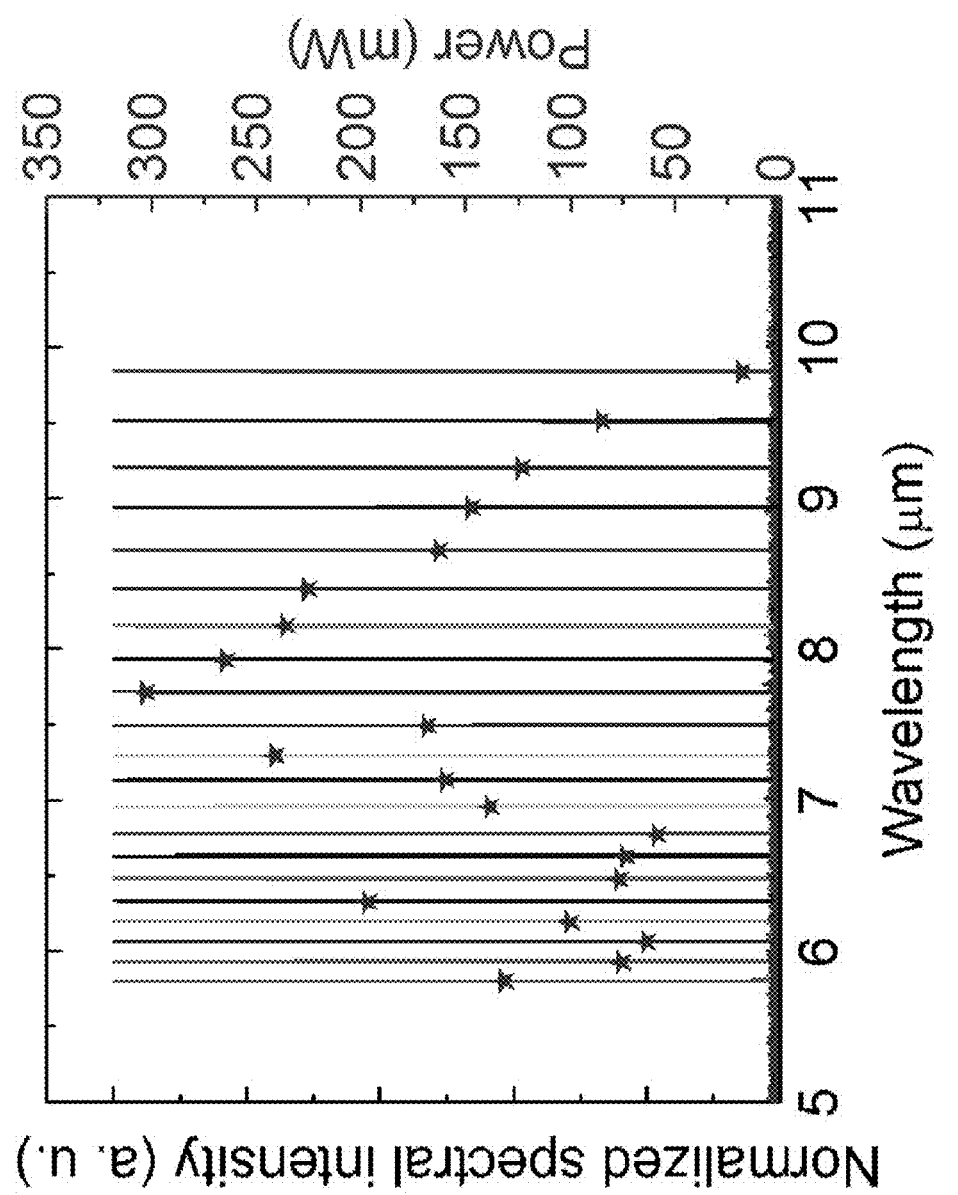
FIG. 4D shows an overlay plot of compiled emission spectra and single mode peak power as a function of wavelength for the QCL device of FIG. 1

Broadband heterogeneous quantum cascade laser core design. Five QC emitters with peak gain at peak emission energies spaced ~20 meV apart were used to form the heterogeneous QCL core with a wavelength targeting range of 6-10 μm. The designed QC emitters are based on strain balanced $Al_{0.63}In_{0.37}As/Ga_{0.35}In_{0.65}As/Ga_{0.47}In_{0.53}As$ material system as illustrated in FIG. 4A. The band offset of strained AlInAs/GaInAs material can be adjusted to an appropriate level by the modulation of Indium incorporation in the ternaries, which can lead to improved performance by suppression of thermal electron leakages to the continuum from upper laser level of a QCL. $Al_{0.63}In_{0.37}As/Ga_{0.35}In_{0.65}As/Ga_{0.47}In_{0.53}As$ QCLs with a band off set of ~800 meV have good performance across the wavelength range 6-10 μm, and they can be incorporated into a heterogeneous QCL active region in a single growth run. When operated at the resonant field, current densities of all QC emitters are nominally ~10 kA/cm$^2$, which is accomplished by adjusting the upper laser level electron lifetime. As shown in FIG. 4B, the gain curve of the heterogeneous QCL core is flat and broad, which allows selection of the laser emitting wavelength over a wide range, using an appropriate feedback mechanism. In order to measure the gain bandwidth and flatness of the designed active region, the grown wafer was characterized via DFB array as described in Bandyopadhyay, N. et al., *Opt. Express* 23, 21159-21164 (2015). The electroluminescence (EL) spectrum of the heterogeneous QCL wafer is shown in FIG. 4C. The EL spectrum has a full width at half maximum (FWHM) of 1050 cm$^{-1}$ around 1420 cm$^{-1}$. As shown in FIG. 4D, single mode DFB emission between 5.8 to 9.9 μm was obtained from a 3 mm long laser bar with both facets AR-coated with 1300 nm Y$_2$O$_3$. The residual reflectivity was below 7% across the 6-10 μm range with a minimum of 1.1% at 8 μm.

The current threshold was relatively flat between 5.8 and 9.0 µm and increased rapidly beyond 9.0 µm. The maximum power output was about 300 mW per facet lasing at 7.7 µm, and most DFBs have power above 100 mW.

Monolithically tunable laser source with single output. As described above, the wafer was subsequently used for the fabrication of monolithically tunable laser source, which consisted of an eight sampled grating distributed feedback (SGDFB) QCL array and a beam combiner section. FIG. 1 shows a perspective view of a schematic of the integrated device and has been further described above. Two electric isolation channels were defined, one isolating the two SGDFB sections, and the other isolating the beam combiner section from the SGDFB array. The ridge waveguide was dry-etched by Induced Coupled Plasma (ICP). A facet view of the ridge waveguide is shown in FIG. 2B and has been further described above. The plasma etching helps produce vertical sidewalls and precise shape for the curved waveguides of the beam combiner. The SGDFB lasers are 5.5 mm long with a ridge width of 10 µm. The primary emitting wavenumber of lasers is spaced by tens of cm$^{-1}$ by controlling the grating period. During operation, one laser is selected and tuned by changing the currents injected to the two laser sections. The separation (gaps) between each laser is as narrow as 100 µm, which is only limited by the wire bonding size. The eight lasers are routed to a single output using a three-stage tree array beam combiner having S-bend waveguides. Given the combiner section length of 3 mm, the bending radius of the S-bend waveguide is designed as large as 1800 µm. The minimum transmission of the S-bend waveguide for wavelengths from 6 to 10 µm is 93% calculated based on beam propagation simulations. A critical consideration for the beam combiner design is the preservation of the fundamental transverse mode. As a solution, the last Y-junction was replaced with a two-in-one funnel combiner as shown in FIG. 3C. The funnel combiner is designed to be wider than the expansion width of the incoming beam and the two input waveguides are directed to the output waveguide. There are both fundamental and higher order transverse modes generated in the output waveguide. The portion of fundamental mode that is coupled into the output waveguide depends on the insertion angle θ between input and output waveguides. With increasing insertion angle θ the total power transmission increases but a lesser portion is coupled into the fundamental mode. In this Example, the insertion angle θ was set at 3.5°. Given this insertion angle, the funnel combiner was 82 µm long and 100 µm wide.

Figure 5:
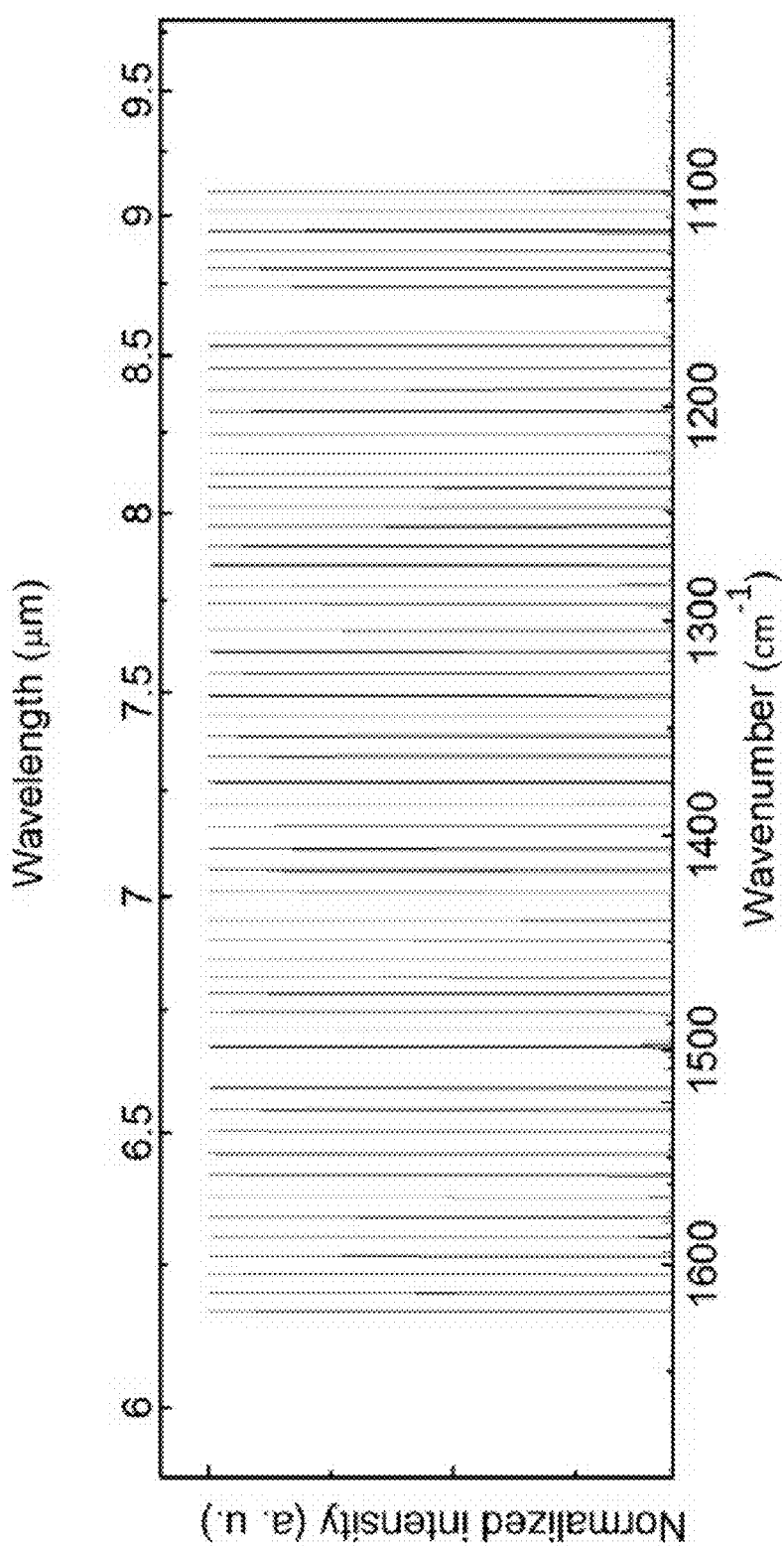
FIG. 5 shows the compiled Vernier tuning spectrum of the QCL device of FIG. 1.

For the SGDFB sections of the grating layer, each comprises a series of short grating regions (grating period and number defined as $\Lambda_g$, $N_g$ respectively) periodically sampled on the two sections with two different sampling periods $Z_1$ and $Z_2$. Both sections of every SGDFB laser are sampled with $N_g$=20 for 16 times, and $\Lambda_g$ ranges from 0.97 to 1.40 µm from laser #1 to #8 (i.e., 104a to 104h in FIG. 1). As only a short region is patterned, the 750 nm-grating layer is all etched to provide a maximum coupling strength. The sampling periods $Z_1$=161.8 µm and $Z_2$=171.5 µm were used for the front and back sections, respectively. The estimated tuning step size is 9.7 cm$^{-1}$ and 9.2 cm$^{-1}$ with front and back section tuning, respectively. In order to use the beam combiner as a single pass amplifier, the front facet was AR-coated with 1300 nm $Y_2O_3$. As described above, tuning spectrum measurements were carried out on a thermoelectric cooler stage at 293 K using a Fourier transform infrared spectrometer (FTIR) at a resolution of 0.125 cm$^{-1}$. Synchronized pulse currents with 100 ns pulse width and 5% duty cycle (500 kHz repetition rate) were first applied to both SGDFB laser sections to reach threshold (~21V). The voltage was kept the same on both sections and was further increased until hit the rollover voltage (~24V, I=1.35$I_{th}$). Because the beam combiner section has the same gain material as the laser sections, a third synchronized pulsed current was applied to the beam combiner section for power amplification. Since the beam combiner facet is AR-coated, single mode emission can be maintained and amplified before the beam combiner reaches a self-lasing condition. In order to maintain a high side mode suppression ratio (SMSR), the combiner voltage was set slightly lower than self-lasing voltage (~19V). Wavelength tuning was realized by applying an additional continuous wave (CW) current to the two SGDFB laser sections. The injected CW currents locally change the section temperature, which leads to the change of the effective refractive index. The tuning of SGDFB lasers is the combination of step-like Vernier tuning, which depends on the CW current difference of two sections, and the continuous tuning of each supermode achieved by changing the current in two sections simultaneously. Each laser in the SGDFB array was selectively biased, and the spectrum of the beam coming out of a single facet was measured. FIG. 5 shows the combined Vernier tuning of 520 cm$^{-1}$ between 6.2 and 9.1 µm. The tuning of each laser is 64, 52, 60, 52, 58, 55, 65 and 45 cm$^{-1}$ for lasers #1 through #8, respectively. The power of each single mode is measured with a thermopile placed in front of the beam combiner facet. With the beam combiner amplification, the overall power is in the mill-watts level. The highest peak power of 5 mW was from laser #6, for which the tuning range was close to a gain peak. The relatively low power compared to DFB laser array was because of a higher threshold of SGDFB lasers ($I_{th,\ SGDFB}$=2.2$I_{th,DFB}$) and the coupling loss in the beam combiner region. The power performance may be improved with better thermal management or stronger grating coupling, which decrease current threshold.

The above Vernier tuning mechanism is not continuous, with a step of 9.2-9.7 cm$^{-1}$ corresponding to the frequency spacing of the supermodes formed by the sampled gratings. However, these gaps can be reduced significantly by changing the CW current in the two sections simultaneously. To illustrate the continuous tuning effect, the tuning of laser #6 between 1237 and 1302 cm$^{-1}$ was chosen (data not shown). The tuning behavior of laser #6 was also evaluated and plots of emission wavelength, side mode suppression ratio (SMSR) and peak intensity as function of the two tuning currents $I_f$ and $I_b$ were obtained (data not shown). From the plots, the eight supermodes are easily recognized. Most spectra had a SMSR above 20 dB with a maximum of 28 dB. The total tuning range amounts to 65 cm$^{-1}$ with maximum continuous tuning of 6.0 cm$^{-1}$. However, full wavelength coverage was not achieved with these lasers, because the continuous tuning range is limited by peak intensity. Based on the spectrum shift measurement of a DFB laser, which is processed from the same wafer, by increasing the thermoelectric cooler (TEC) temperature, a tuning coefficient of 0.1 cm$^{-1}$/K is estimated. This means that a 60-degree increase in temperature makes the laser unable to reach threshold. The continuous tuning gaps may be bridged by decreasing the supermode space via increasing the sampling period length $Z_1$ and $Z_2$.

Figure 6A:
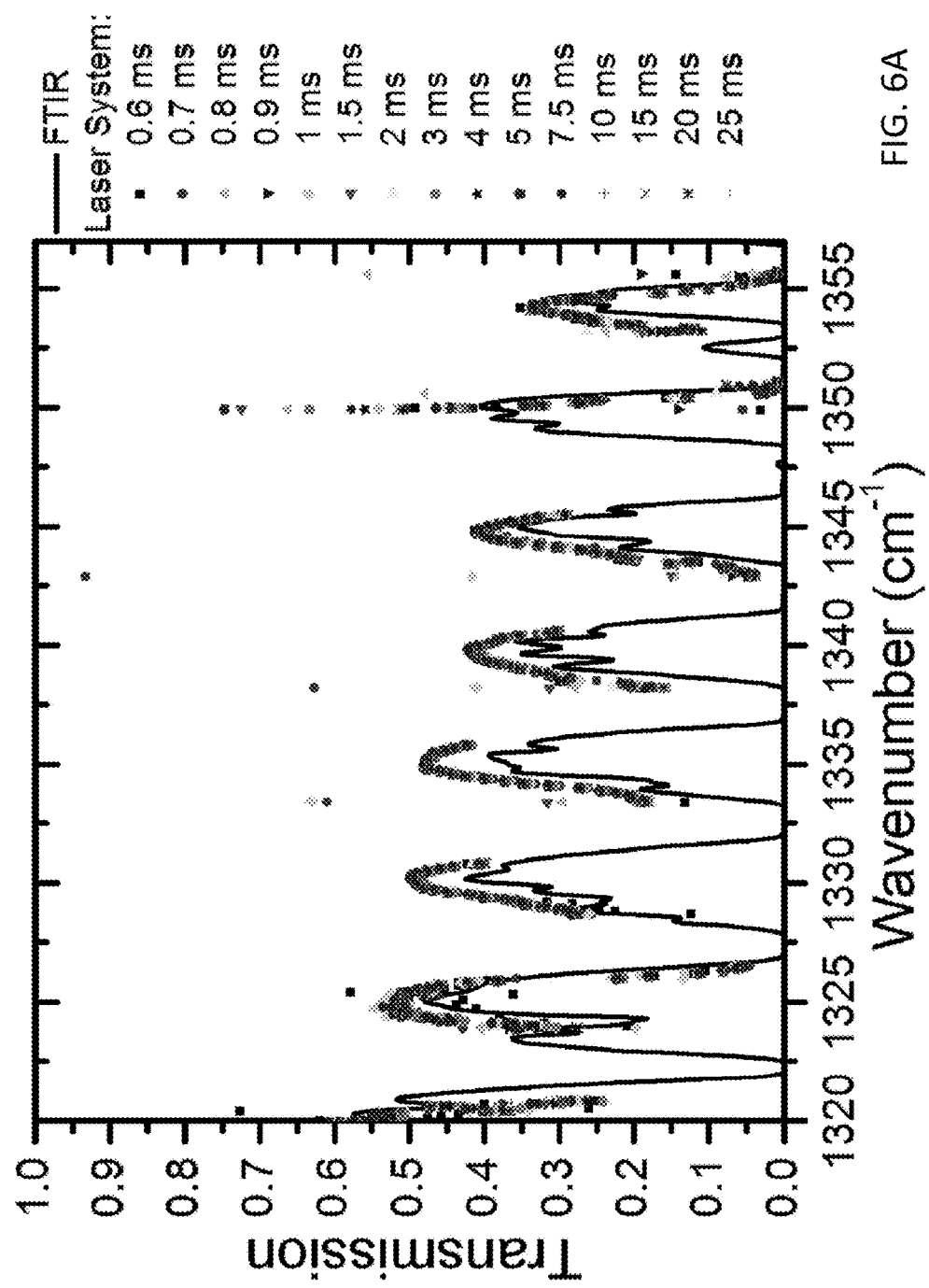
FIG. 6A shows a comparison of 15 transmission spectra taken with delay times of 0.6 to 25 ms after changing the laser wavelength with the expected FTIR signal.

Broadband absorption spectroscopy of methane. In order to test the tuning speed of the device, a self-contained tunable laser system was designed and built as described above. This system works off of a single 48V DC power supply and contains all of the electronics necessary to drive the individual lasers within the array and coordinate the driving of the laser array and produce the desired wavelength. The laser comes out of as single collimated output from the front of the system. The system was calibrated using custom written automatic calibration software to perform nearly 43,000 scans; spectra were recorded with a FTIR for different lasers and DC current combinations. For each of the lasers in the array, a colormap was made showing the peak wavelength as function of front and back section currents (data not shown). This was then used to generate optimized paths through the data and create a table of pre-calibrated scan paths. The software was able to interpolate along these paths with a resolution of better than 0.1 nm. In order to use the system for chemical spectroscopy, a wavelength region of interest is selected, and a scan is generated by specifying start, stop, and step conditions for the scan. In order to support high speed scanning, each discrete scan-state is downloaded to a dedicated random access memory (RAM) chip on the control board. A crystal oscillator, a phase-locked loop, and frequency divider within the control field programmable gate array (FPGA) are then used to step through the states stored in the RAM. As the electronic hardware supports a scan rate of up to 32,000 Hz, the tuning speed is only limited by the laser stabilization delay after changing the wavelength. As described above, a spectroscopy measurement setup was built to determine the delay time. The gas cell was first scanned with a vacuum FTIR in order to obtain a reference spectrum. Then 15 spectra were taken with delay times of 0.6 to 25 ms after changing the laser wavelength. FIG. 6A compares those scans (dots) with the expected FTIR signal (solid line). For delays of 900 µs or greater, these data track the expected FTIR data. This suggests that the system can scan at about 1 kHz. Also measured was the time-dependent variance of the signal for 60 random gas-cell transmission data points (data not shown). All the lasers become stable after 1ms. Below 1 ms, the variance increases dramatically, which sets an upper limit on the scan speed of 1 kHz as well.

Figure 6B:
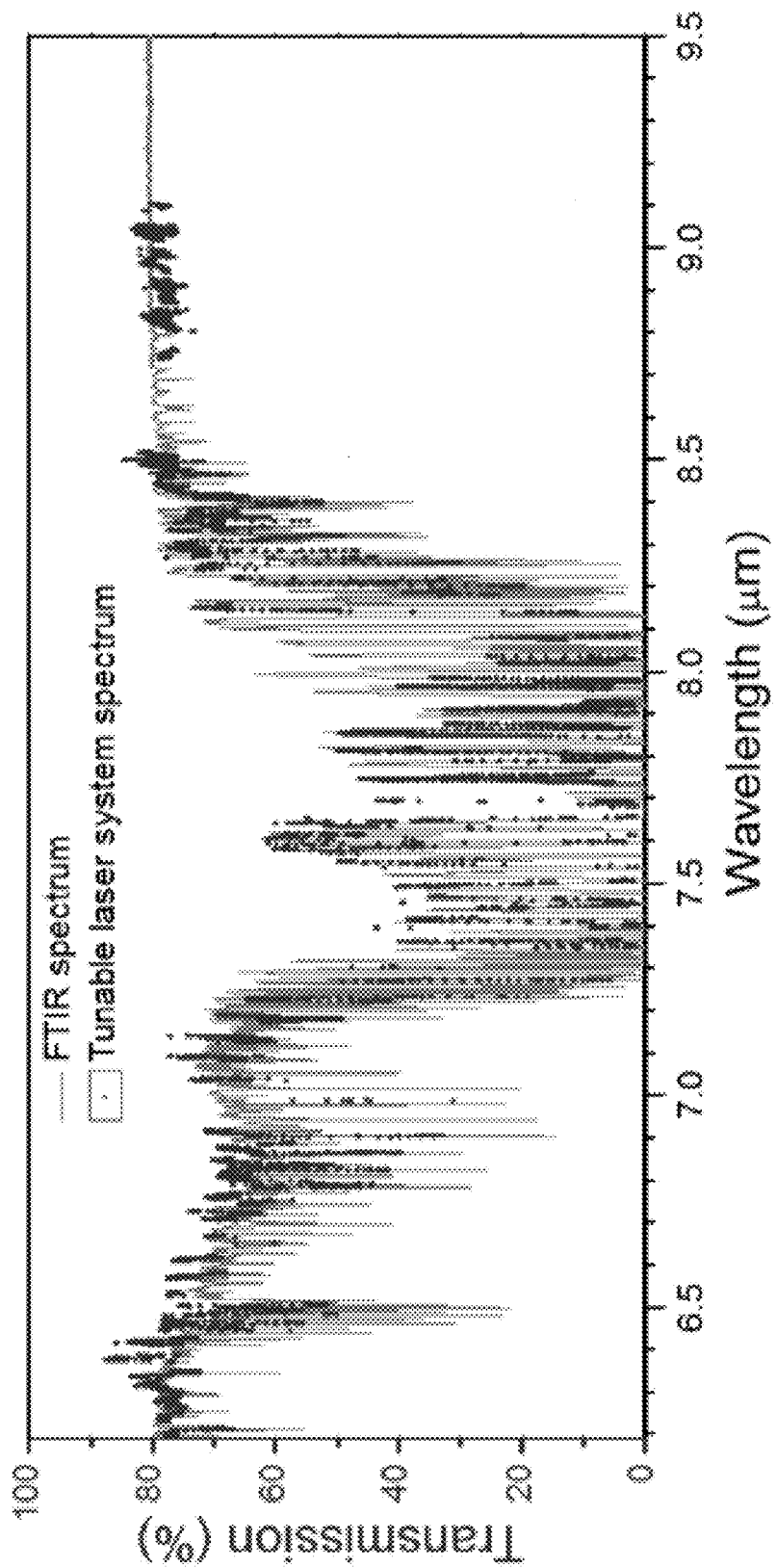
FIG. 6B shows a comparison of the spectrum measured with the QCL device of FIG. 1 to the expected spectrum measured with the FTIR.
Figure 6C:
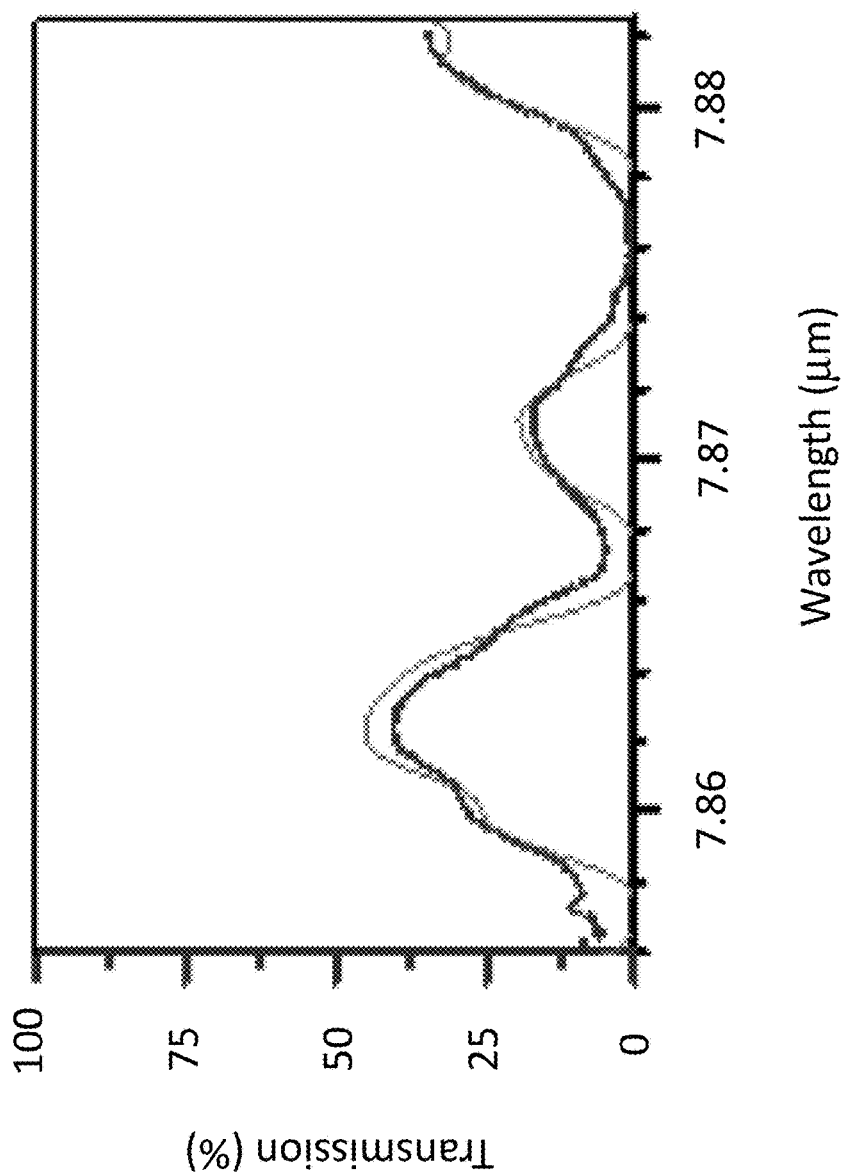
FIG. 6C is an inset showing a zoomed-in region of FIG. 6B showing the excellent agreement between the spectrum measured with the QCL device of FIG. 1 and the FTIR spectrum.

The tunable laser system was scanned from 6.2 µm to 9.1 µm with a step size of 0.1 nm at a scan rate of 512 Hz, which is limited by the detection electronics. Because the tunable device has a single output and a lens installed, with a path length of 15 cm all eight lasers in the array can be scanned without needing to adjust any alignments. FIG. 6B shows a comparison of the reference spectrum (grey) to that measured with the tunable laser system (points). In general, the tunable laser system is able to accurately measure the spectrum of methane. In particular, FIG. 6C shows excellent agreement with some of the fine spectral features.

Conclusion

In conclusion, a tunable QCL source from 6.2 µm to 9.1 µm (520 cm$^{-1}$) was demonstrated using an eight-laser SGDFB array integrated with an on-chip beam combiner based on a five-emitter heterogeneous QCL wafer. A compact tunable laser system was built to drive the individual lasers within the array and coordinate the driving of the laser array to produce desired wavelength. The system was able to scan up to 1 kHz, which is limited by the stabilization delay after changing the wavelength. The spectral measurement of methane form 6.2 µm to 9.1 µm shows good agreement with FTIR measurement. This broadly tunable QCL source with no moving part can be used in MIR spectroscopy and chemical sensing.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A monolithic, wavelength-tunable quantum cascade laser (QCL) device comprising:
    a substrate;
    an array of QCLs formed on the substrate, each QCL comprising a first QCL section and a second QCL section electrically isolated from the first QCL section, each QCL comprising
    a quantum cascade (QC) core comprising n QC emitters wherein n is an integer of 2 or greater, each QC emitter comprising at least one stage comprising a superlattice of quantum well layers and barrier layers defining an active region configured to generate light having a wavelength λ under an applied bias voltage, wherein each QC emitter is configured to generate light having a different wavelength such that the QC core generates light having wavelengths $\lambda_1$ to $\lambda_n$;
    a grating layer over the QC core, the grating layer configured to provide optical feedback for a selected wavelength of light generated by the QC core and to produce lasing at the selected wavelength of light, the grating layer comprising
        a first sampled grating distributed feedback grating (SGDFB) section associated with the first QCL section, the first SGDFB grating section comprising grating regions periodically alternating with gratingless regions and characterized by a grating period $\Lambda_g$, a grating number $N_g$, and a first sampling period $Z_1$; and
        a second SGDFB section associated with the second QCL section, the second SGDFB grating section comprising grating regions periodically alternating with gratingless regions and characterized by the grating period $\Lambda_g$, the grating number $N_g$, and a second sampling period $Z_2$, wherein the grating layer of each QCL is characterized by a different grating period $\Lambda_g$; and
    a cladding layer over the QC core; and
    an optical beam combiner formed on the substrate electrically isolated from the array of QCLs, the optical beam combiner configured to convey and amplify the laser light produced from each QCL to a single exit aperture, the optical beam combiner comprising
        a plurality of input waveguide structures, each input waveguide structure optically coupled to an associated QCL;
        a coupler waveguide structure optically coupled to the plurality of input waveguide structures; and
        a single output waveguide structure having the single exit aperture from which laser emission exits, wherein each input waveguide structure, the coupler waveguide structure and the single output waveguide structure comprise the QC core and the cladding layer.

2. The device of claim 1, wherein n=5 such that the QC core comprises five QC emitters.

3. The device of claim 2, wherein the array of QCLs comprises 8 QCLs.

4. The device of claim 1, wherein the substrate is InP and the QC emitters comprise AlInAs/GaInAs heterostructures.

5. The device of claim 1, wherein the grating layer is a buried grating layer.

6. The device of claim 1, wherein the optical beam combiner is configured as a tree-array combiner comprising one or more intermediate waveguide structures and one or more intermediate coupler waveguide structures between the plurality of input waveguide structures and the coupler waveguide structure.

7. The device of claim 1, wherein the optical beam combiner is configured as a funnel combiner.

8. The device of claim 1, wherein the single exit aperture comprises an antireflective coating thereon.

9. The device of claim 1, wherein the device is configured to provide laser emission in the range of from about 3 μm to about 12 μm.

10. The device of claim 9, wherein the device is configured to provide laser emission in the range of from about 6 μm to about 10 μm.

11. The device of claim 10, wherein the device is characterized by a wavelength tuning range of at least about 500 cm$^{-1}$, a wavelength tuning step size of about 1.0 nm or less, or both.

12. A system comprising the device of claim 1 operably coupled to electrical components and a controller configured to control the application of a bias voltage to the first and second QCL sections of each QCL and the optical beam combiner.

13. A sensor comprising the system of claim 12, a sample cell mounted to the device and configured to contain a gas, and a detector mounted to the sample cell.

* * * * *